US011160905B2

(12) United States Patent
Beres et al.

(10) Patent No.: US 11,160,905 B2
(45) Date of Patent: Nov. 2, 2021

(54) CONNECTIVE TISSUES, SUCH AS BONE, DENTIN OR PULP, REGENERATIVE MATERIAL COMPRISING CALCIUM SILICATE

(71) Applicants: SEPTODONT OU SEPTODONT SAS OU SPECIALITES SEPTODONT, Saint Maur des Fossés (FR); UNIVERSITÉ PARIS, Paris (FR); INSERM (INSTITUT NATIONAL DE LA SANTÉ ET DE LA RECHERCHE MÉDICALE), Paris (FR); SORBONNE UNIVERSITE, Paris (FR); ASSISTANCE PUBLIQUE—HOPITAUX DE PARIS, Paris (FR)

(72) Inventors: Fleur Beres, Saint-Ouen (FR); Gilles Richard, Crosne (FR); Arnaud Dessombz, Paris (FR); Stéphane Simon, Bois Guillaune (FR); Juliane Isaac, Paris (FR)

(73) Assignees: SEPTODONT OU SEPTODONT SAS OU SPECIALITES SEPTODONT, Saint Maur des Fossés (FR); UNIVERSITE DE PARIS, Paris (FR); INSERM (INSTITUT NATIONAL DE LA SANTÉ ET DE LA RECHERCHE MÉDICALE), Paris (FR); SORBONNE UNIVERSITE, Paris (FR); ASSISTANCE PUBLIQUE—HOPITAUX DE PARIS, Paris (FR)

(*) Notice: Subject to any disclaimer, the term of this patent is extended or adjusted under 35 U.S.C. 154(b) by 0 days.

(21) Appl. No.: 16/604,442

(22) PCT Filed: Apr. 13, 2018

(86) PCT No.: PCT/EP2018/059563
§ 371 (c)(1),
(2) Date: Oct. 10, 2019

(87) PCT Pub. No.: WO2018/189384
PCT Pub. Date: Oct. 18, 2018

(65) Prior Publication Data
US 2020/0155725 A1 May 21, 2020

(30) Foreign Application Priority Data

Apr. 13, 2017 (EP) .................................... 17305444
Nov. 24, 2017 (EP) .................................... 17203635

(51) Int. Cl.
*A61L 27/44* (2006.01)
*A61L 27/20* (2006.01)
(Continued)

(52) U.S. Cl.
CPC .............. *A61L 27/44* (2013.01); *A61L 27/20* (2013.01); *A61L 27/222* (2013.01); *A61L 27/24* (2013.01);
(Continued)

(58) Field of Classification Search
None
See application file for complete search history.

(56) References Cited

U.S. PATENT DOCUMENTS 6,214,048 B1   4/2001 Ito et al.
8,506,985 B2 * 8/2013 Garcia De Castro Andrews ........ A61F 2/02
                                                                          424/426

(Continued)

FOREIGN PATENT DOCUMENTS

| EP | 0555807 A1 | 8/1993 |
| WO | 0045871 A1 | 8/2000 |
| WO | 2008076671 A2 | 6/2008 |
| WO | 2017031906 A1 | 3/2017 |

OTHER PUBLICATIONS

A.L. Oliveira, et al., "Biomimetic Coating of Starch Based Polymeric Foams Produced by a Calcium Silicate Based Methodology", Key Engineering Materials, vol. 240-242, Jan. 1, 2003, pp. 101-104, XP055411096.

(Continued)

*Primary Examiner* — Celeste A Roney
(74) *Attorney, Agent, or Firm* — Maier & Maier, PLLC

(57) ABSTRACT

A regenerative material in the connective tissues (such as bone, dentin or pulp) regeneration field. More precisely, a connective tissue regenerative material, preferably a bone, dentin or pulp regenerative material, including: a porous polymer matrix having interconnected pores; and non-hydrated calcium silicate particles; wherein: the polymer matrix is anhydrous; the non-hydrated calcium silicate particles have a $d_{50}$ granulometry, preferably ranging from 0.05 μm to less than the average diameter size of the pores of the matrix; and the non-hydrated calcium silicate particles being coated on the inside walls of the pores of the matrix. Also, a method for preparing the connective tissue regenerative material and uses of the regenerative materials, such as in the dental field; especially, for providing regenerative materials with improved biomechanical and osteoinductive properties (i.e. good migration, adhesion and proliferation of cells; enhanced mechanical properties; and optimal and controlled biodegradability).

20 Claims, 8 Drawing Sheets

(51) Int. Cl.
*A61L 27/22* (2006.01)
*A61L 27/24* (2006.01)
*A61L 27/26* (2006.01)
*A61L 27/56* (2006.01)

(52) U.S. Cl.
CPC ............. *A61L 27/26* (2013.01); *A61L 27/56* (2013.01); *A61L 2300/412* (2013.01); *A61L 2430/02* (2013.01); *A61L 2430/12* (2013.01)

(56) References Cited

U.S. PATENT DOCUMENTS

| | | | |
|---|---|---|---|
| 8,518,123 B2 * | 8/2013 | Jensen | A61L 27/56 623/23.59 |
| 9,304,359 B2 * | 4/2016 | Nagami | G02F 1/133514 |
| 2009/0010983 A1 * | 1/2009 | Melvik | A61L 27/48 424/422 |
| 2011/0160104 A1 * | 6/2011 | Wu | E21B 43/267 507/269 |
| 2018/0028720 A1 * | 2/2018 | De Groot-Barrere | A61L 27/46 |

OTHER PUBLICATIONS

International Search Report, dated May 25, 2018, in corresponding International Application No. PCT/EP2018/059563, 3 pages.

* cited by examiner

CONNECTIVE TISSUES, SUCH AS BONE, DENTIN OR PULP, REGENERATIVE MATERIAL COMPRISING CALCIUM SILICATE

FIELD

The present invention relates to a regenerative material in the connective tissues (such as bone, dentin or pulp) regeneration field. More precisely, the present invention relates to an anhydrous connective tissue regenerative material, preferably a bone, dentin or pulp regenerative material, comprising a porous polymer matrix and calcium silicate particles. The present invention also relates to method for preparing said regenerative material. The present invention also concerns uses of said regenerative materials, such as for example in the dental field; especially, for providing regenerative materials with improved biomechanical and osteoinductive properties (i.e. good migration, adhesion and proliferation of cells; enhanced mechanical properties; and optimal and controlled biodegradability).

BACKGROUND

Tissue loss or failure of vital organs (resulting from pathologic or traumatic source) is a huge public health problem. Especially, in the dental field, dental bone defects resulting from severe periodontal diseases, dental extractions or tumor resections, lead to an alveolar bone resorption in the absence of treatment. This bone resorption causes in one hand, functional, phonetic and anesthetic issues; and in another hand, leads to an insufficient bone volume for allowing the implementation of an implant.

Most of the time, the only therapeutic solution for tissue loss or failure of vital organs concerns a transplant.

First, the transplantation of autogenous bone (i.e. bone taken from the patient himself) remains the material of choice due to its osteoconductive, osteoinductive and osteogenic properties. However, the small bone regeneration obtained, the risks of graft resorption and the painful postoperative cares still are the main drawbacks of this therapeutic solution.

Another therapeutic solution concerns the transplantation of a bone obtained from a donor. However, the limited number of donors, the risk of graft rejection for immunological reasons, the risk of transmission of pathogenic agents and the obligation for the patient to receive a specific medical treatment led the research community to find alternative solution.

The use of synthetic restorative materials is well-accepted for many years. This class of materials is used for reconstructing a tissue either by strengthening a tissue structure or by filling a substance loss. Among them, several bone substitute materials have been developed such as biomaterials comprising ceramic particles. For instance, EP 0 555 807 and U.S. Pat. No. 6,214,048 have reported a bone substitute material prepared by mixing an animal bone powder with apatite.

So far, the restorative procedures including the use of bone substitute materials, are restricted to the replacement of damaged tissues by synthetic materials and do not provide a solution for regenerating these damaged tissues. These drawbacks combined with the hostile and infected environment of oral cavity often lead to failure.

In this context, tissue engineering emerged as one of the most promising way for bone regenerative medicine and dentistry. This field aims to replace, maintain or improve the function of human tissues thanks to tissue substitutes including biological elements. Thus, alternative substitute materials have been developed for inducting or stimulating the osteoinductive properties of these materials to be implanted into the body. However, most of the time, the therapeutic solutions require that the bone medical implant comprises osteoinductive factors (WO 00/45871 and WO 2008/076671).

In light of the background, there is still a need for providing improved restorative materials 1) that directly interact with the biological medium such as for example, tissues; and 2) having improved biomechanical and osteostimulation properties, especially without the need of additional conventional osteoinductive factors (such as biological osteoinductive factors). Especially, there is a need for providing biocompatible and bioresorbable regenerative materials having a concomitant progressive resorption with the induced bone growth while keeping a good structural stability in vivo. Connective tissues such dentin or pulp, substitute material need to overcome the same drawbacks as those described for current bone substitute materials. Thus, there is still a need for providing a connective tissue (such as bone, dentin or pulp) regenerative material.

Furthermore, there is also a need for providing a regenerative material having resorption kinetics compatible with regeneration kinetics of the tissues to be replaced.

Surprisingly, the Applicant has shown that a three-dimensional anhydrous matrix of biopolymer (such as chitosan, for example) comprising non-hydrated calcium silicate particles allows solving the drawbacks as described above.

Advantageously, non-hydrated calcium silicate particles adjunction improves biological properties of connective tissues (such as bone, dentin or pulp) regenerative material. Advantageously, connective tissues (such as bone, dentin or pulp) regenerative material has a pore diameter higher than the cell diameter so that said bone, connective tissues such as dentin or pulp, regenerative material improves the cell migration. Advantageously, connective tissues such as bone, dentin or pulp, regenerative material is rough enough to improve and favor the cell adhesion and proliferation. Advantageously, the materials of the invention have also elastic properties in accordance to the hard tissue structures, so that said materials maintain their physical integrity when used.

SUMMARY

This invention thus relates to a connective tissue regenerative material, preferably a bone, dentin or pulp regenerative material, comprising:
a porous polymer matrix having interconnected pores; and
calcium silicate particles;
wherein:
said polymer matrix is anhydrous;
said calcium silicate particles are non-hydrated;
said non-hydrated calcium silicate particles have a $d_{50}$ granulometry preferably ranging from 0.05 μm to less than the average diameter of the pores of the matrix; and
said non-hydrated calcium silicate particles being coated on the inside walls of the pores of the matrix.

According to one embodiment, the porous polymer matrix comprises or consists of at least one polymer selected from biodegradable and/or biocompatible polymer; preferably said polymer is selected from polyesters, polysaccharides, polypeptides and proteins; more preferably from the group selected from chitosan, chitin, alginate, collagen, hyaluronic acid, poly(lactic acid), poly(glycolic acid), poly(caprolactone), gelatin or any copolymers thereof.

According to one embodiment, the polymer is chitosan or a mixture of chitosan and alginate.

According to one embodiment, the connective tissue regenerative material further comprises at least one additive; preferably selected from fibers such as alginate fibers; and radio-opacifiers such as bismuth oxide, strontium carbonate, strontium phosphate, barium sulfate, tantalum oxide, cerium oxide, tin oxide, zirconium oxide compounds; and pigments such as yellow, red and brown iron oxide.

According to one embodiment, the matrix is structured in sheets.

According to one embodiment, the inter-sheet distance ranges from 50 to 150 µm.

According to one embodiment, the calcium silicate particles are selected from dicalcium silicate particles, tricalcium silicate particles or any mixtures thereof; preferably the calcium silicate particles are tricalcium silicate.

According to one embodiment, the average pore diameter ranges from higher than 50 µm; preferably the average pore diameter ranges from 75 µm to 900 µm; more preferably the pore diameter ranges from 100 µm to 300 µm.

The invention also refers to a process for manufacturing the connective tissue regenerative material of the invention, comprising a step for contacting an anhydrous porous polymer matrix with a suspension of non-hydrated calcium silicate particles in an anhydrous polar solvent.

According to one embodiment, the process of the invention further comprises a preliminary step for preparing the anhydrous porous polymer matrix, said step comprising:
(i) preparing an aqueous solution comprising:
at least one polymer, preferably a biodegradable and/or biocompatible polymer; preferably selected from polyesters, polysaccharides, polypeptides and proteins; more preferably from the group selected from chitosan, chitin, alginate, collagen, hyaluronic acid, poly(lactic acid), poly(glycolic acid), poly(caprolactone), gelatin or any copolymers thereof; and
optionally an acid;
(ii) pouring the solution in a mold;
(iii) removing water.

According to one embodiment, the means for removing water is selected from lyophilizer, heat evaporator and vacuum evaporator.

According to one embodiment, when the polymer is chitosan or chitin, the aqueous solution comprises an acid, preferably an organic acid, more preferably acetic acid.

According to one embodiment, the polar solvent is selected from acetonitrile, dichloromethane, tetrahydrofuran, ethyl acetate, dimethylformamide, dimethylsulfoxide, acetone, methanol, ethanol isopropyl alcohol and acetic acid, preferably the polar solvent is acetonitrile.

The present invention also refers to a connective tissue regenerative material of the invention, for use in the treatment of connective tissue loss in a patient in need thereof.

The present invention also refers to an implant comprising the connective tissue regenerative material of the invention.

Detailed Descriptions

Figure 1:
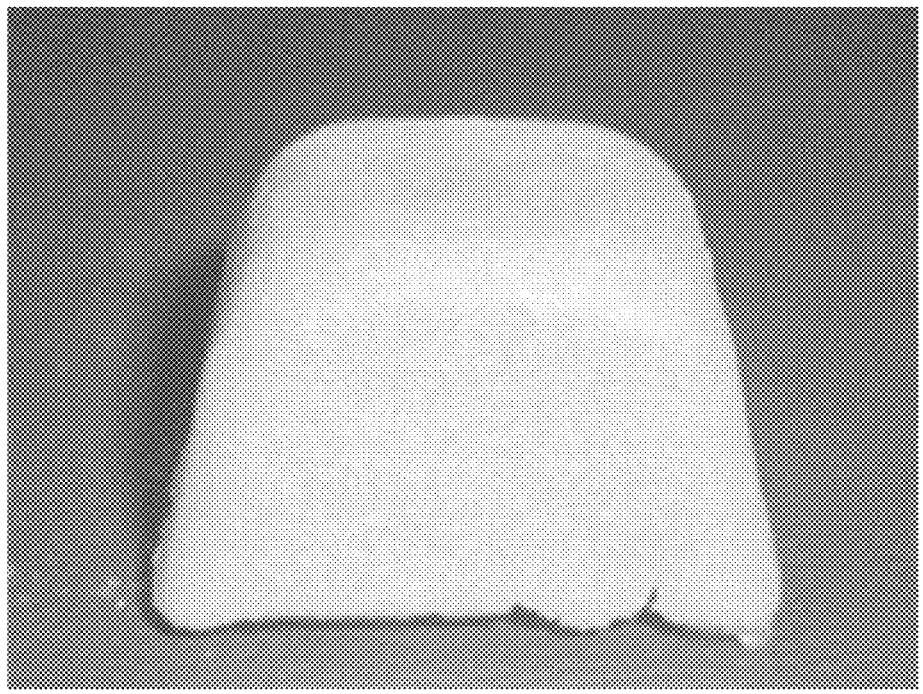
FIG. 1 is a photograph showing a chitosan porous biopolymer matrix.

In the present invention, the following terms have the following meanings:
"About" preceding a figure means plus or less 10% of the value of said figure;
"Acetonitrile": refers to the compound having the formula $CH_3CN$;

"Acid": refers to any organic or mineral compound able to accept electronic doublet and deliver hydronium ion (H+);

"Alginate": refers to salts of alginic acid. Alginic acid, which is isolated from seaweed, is a polyuronic acid made up of two uronic acids: D-mannuronic acid and L-guluronic acid. Alginic acid is substantially insoluble in water. It forms water-soluble salts with alkali metals, such as sodium, potassium, and, lithium; magnesium; ammonium; and the substituted ammonium cations derived from lower amines, such as methyl amine, ethanol amine, diethanol amine, and triethanol amine. The salts are soluble in aqueous media above pH 4, but are converted to alginic acid when the pH is lowered below about pH 4. A thermo-irreversible water-insoluble alginate gel is formed in the presence of gel-forming ions, e.g. calcium, barium, strontium, zinc, copper, aluminum, and mixtures thereof, at appropriate concentrations. The alginate gels can be solubilized by soaking in a solution of soluble cations or chelating agents for the gel-forming ions, for example EDTA, citrate and the like;

"Anhydrous" or "non-hydrated": refers to any compound or material that does not contain any water. Especially, the term "non-hydrated" further means that said compound or material has not been contacted with any water molecules;

"Biocompatible": refers to any material eliciting little or no immune response in a given organism, or is able to integrate with a particular cell type or tissue;

"Biodegradable": refers to materials that are bioresorbable and/or degrade and/or break down by mechanical degradation upon interaction within a physiological environment into components that are metabolizable or excretable;

"Biopolymer": refers to any bio-sourced polymer;

"Bone": refers to rigid organs that constitute part of the endoskeleton of vertebrates. For instance, the term "bone" encompasses bone, mandibular bone, spongious bone and membranous bone;

"Connective tissues loss": refers to any condition dealing with a loss of connective tissues such as for example, bone, dentin or pulp, density. For example, the density loss may occur from resorption, surgery, tooth extraction, infections, trauma, diseases and/or aging such as joints aging;

"Connective tissues regenerative material": refers to any material used for facing connective tissues (such as bone, dentin or pulp) lossable to induce in vivo the formation of a new self-generating tissue;

"Calcium silicate particle": refers to an assembly comprising one or more calcium silicate compounds. The terms "calcium silicate particle" also include assemblies constituted by one or more calcium silicate compounds;

"Chitosan": refers to a product obtained from the deacetylation of chitin. The difference between chitosan and chitin is the acetylation degree: above 50% the polymer is chitin, below 50% the polymer is chitosan;

"Chitin": refers to a polysaccharide of N-acetylglucosamine and glucosamine;

"Coating": refers to any partial or total covering of a substance on a surface;

"Collagen": refers to a protein comprising a right-handed bundle of three parallel, left-handed polyproline II-type helices;

"Connective tissue": refers to any tissue that supports and binds other body tissue and parts. A connective tissue is a dense, containing large numbers of cells and large amounts of intercellular material. The intercellular material is composed of fibers in a matrix or ground substance that may be liquid, gelatinous, or mineralized, such as in bone and cartilage. Connective tissue fibers may be collagenous or elastic. The matrix or ground material surrounding fibers and cells is a dynamic substance, susceptible to its own special diseases. The terms "connective tissues" include bone tissue, cartilage tissue, dense connective tissue and fibrous tissue. The terms "connective tissues" include soft connective tissues and/or mineralized connective tissues. In one embodiment, the connective tissue is bone, dentine and/or pulp;

"$d_{50}$ granulometry": refers in the present invention to the $d_{50}$ granulometry of calcium silicate particles. The value "$d_{50}$" means that 50% of calcium silicate particles have a diameter lower than said value. In the present invention, granulometry is measured by an apparatus Beckman-Coulter LS230 Particle Size Analyzer with a SVM module. According to one embodiment, granulometry is measured by granulolaser;

"Deacetylation degree": refers to the ratio between the number of removed acetyl ($CH_3CO$—) functions by the number of initial acetyl functions in a chemical compound. For example, chitosan is produced by deacetylation of chitin and its deacetylation degree may range from more than 50% to 100%;

"Dicalcium silicate": refers to the chemical compound of formula $Ca_2SiO_4$;

"Freezing": refers to a process for providing a frozen product;

"Gelatin": refers to a heterogeneous mixture of proteins of high molecular weight derived from collagen and extracted from animals raw materials (such as for example skin, tendons, ligaments, bones);

"Hyaluronic acid": refers to a polysaccharide of glycosaminoglycan family having two repeating units: $\beta$-(1,3)-D gluronic acid and $\beta$-(1,4)-N-acetyl-D-glucosamine acid. This polysaccharide is largely present in human body, especially in connective tissue, epithelial and nervous;

"Implant": refers to any foreign body voluntarily introduced into a body;

"Inter-sheet distance": refers to the shortest distance between two sheets of the polymer matrix;

"Interconnected pores" or "opened pores": refers to a network of pores;

"Lyophilizing": refers to a process of drying a previously frozen product by sublimation. The sublimed solvent may be water or alcohol;

"Matrix": refers to any network of a material. In the present invention, this term refers to any polymer network;

"Mold": refers to any hollow container used to give shape to a material;

"Monolayer": refers to any compact two-dimensional assembly consisting of atoms or molecules. Especially, in the present invention, the monolayer preferably refers to a layer consisting of calcium silicate compounds. Preferably, the thickness of the layer is about the $d_{50}$ granulometry of calcium silicate compounds;

"Organic acid": refers to any organic compound having at least one carboxyl group (—COOH) or sulfonic group (—$SO_3H$);

"Patient": refers to any warm-blooded animal, preferably human, who/which is awaiting for, or is receiving medical care or is/will be the object of a medical procedure;

"Polar solvent": refers to any solvent whose electric charges are unequally distributed so that the resulting molecular dipole moment is not zero;

"Poly(caprolactone)": refers to a polymer obtained from the polymerization of caprolactone;

"Polyester": refers to any polymer comprising a repeating unit with at least one ester function. In the present invention, the term "polyester" includes any polymer resulting from a polycondensation reaction between a diacid compound and a dialcohol compound or any polymer resulting from the transesterification of a polyester;

"Poly(glycolic acid)", "poly(glycolide)" or "PGA": refers to refers to any polymer obtained from the polymerization of either glycolic acid or the cyclic ester diester glycolide;

"Poly(lactic acid)", "polylactide" or "PLA": refers to any polymer obtained from the polymerization of either lactic acid or the cyclic diester, lactide;

"Polymer": refers to any chain or material having a high molecular weight and resulting from the multiple repetition of a repeating unit (monomer), said monomers being covalently linked each other;

"Polypeptide": refers to a linear polymer of at least 50 amino acids linked together by peptide bonds;

"Polysaccharide": refers to any polymeric carbohydrate molecule composed of long chains of monosaccharide units bound together by glycosidic linkages; which may be linear or branched. Examples include starch, glycogen, cellulose and chitin;

"Porous": refers to a compound comprising macropores (an average pore diameter equal or higher than 50 nm). In the present invention, "porous" preferably refers to compound comprising macropores having a pore diameter higher than 50 µm; preferably the average pore diameter ranges from 75 µm to 900 µm; preferably ranging from 75 µm to 750 µm; more preferably ranging from 100 µm to 300 µm; more preferably ranging from 100 µm to 200 µm. In the present invention, the pore diameter is measured by the well-known techniques of the skilled artisan such as for example, Brunauer-Emmett-Teller Method (BET), microtomography, Scanning Electron Microscopy (SEM);

"Pulp": refers to the connective tissue located inner structure of a tooth, including cells, extracellular matrix, nerve and blood vessels;

"Protein": refers to a functional entity formed of one or more peptides or polypeptides;

"Restorative": refers to any osteoconductive material for its implantation in a human body that aims to reconstruct a tissue by either strengthening the tissue structure or filling a substance loss;

"Regenerative material": refers to a material able to induce in vivo the formation of a new self-generating tissue;

"Sheet": refers to any large, wide amount of flat element in a material;

"Suspension": refers to any liquid in which solid particles are dispersed;

"Treatment" or "Treating": refers to therapeutic treatment wherein the object is to cure or slow down (lessen) the targeted pathologic condition or disorder. A subject or mammal is successfully "treated" for the condition or disorder if, after receiving the connective tissues (such as bone, dentin or pulp) regenerative material of the present invention, the patient shows observable and/or measurable reduction in one or more of the symptoms associated with the specific disease or condition; and improvement in quality of life issues. The above parameters for assessing successful treatment and improvement in the disease or conditions are readily measurable by routine procedures familiar to a physician;

"Tricalcium silicate": refers to the chemical compound of formula $Ca_3SiO_9$.

Regenerative Material

As noted above, the present invention relates to a regenerative material. In one embodiment, the regenerative material of the invention provides a mineralized tissue. In one embodiment, the material is a connective tissue regenerative material. In one embodiment, the material is a bone, dentin or pulp regenerative material.

According to one embodiment, the present invention relates to a connective tissue (such as bone, dentin or pulp) regenerative material comprising or consisting of:
a porous polymer matrix having interconnected pores; and
non-hydrated calcium silicate particles;
wherein:
said polymer matrix is anhydrous;
said non-hydrated calcium silicate particles have a $d_{50}$ granulometry ranging from 0.05 µm to less than the average diameter size of the pores of the matrix, preferably from 0.05 µm to 50 µm; and
said non-hydrated calcium silicate particles form a coating inside the pores of the matrix.

According to one embodiment, the connective tissue (such as bone, dentin or pulp) regenerative material comprises or consists of:
a porous chitosan-alginate matrix having interconnected pores; and
non-hydrated tricalcium silicate particles;
wherein:
said chitosan-alginate matrix is anhydrous;
said particles having a $d_{50}$ granulometry ranging from 0.05 µm to less than the average diameter size of the pores of the matrix, preferably from 0.05 µm to 50 µm; and said non-hydrated calcium silicate particles form a coating inside the pores of the matrix.

According to one embodiment, the present invention relates to a connective tissue regenerative material, preferably a bone, dentin or pulp regenerative material, comprising:
a porous polymer matrix having interconnected pores; and
calcium silicate particles;
wherein:
said polymer matrix is anhydrous and is selected from biodegradable and/or biocompatible polymer, said polymer precipitating in an aqueous solution having a pH above 6.5, preferably above 7;
said calcium silicate particles are non-hydrated;
said non-hydrated calcium silicate particles have a $d_{50}$ granulometry preferably ranging from 0.05 µm to less than the average diameter of the pores of the matrix;
said non-hydrated calcium silicate particles being coated on the inside walls of the pores of the matrix; and
provided that calcium silicate particles are not monocalcium silicate ($CaSiO_3$).

According to one embodiment, the connective tissue regenerative material is not a collagen matrix comprising hydroxyapatite. According to one embodiment, the matrix does not comprise hydroxyapatite. According to one embodiment, the connective tissue regenerative material is not a gelatin-chitosan matrix comprising calcium nitrate. According to one embodiment, the connective tissue regenerative material does not comprise a silicon compound. According to one embodiment, the matrix is a three-dimensional material. According to a first embodiment, the matrix is not a liquid. According to one embodiment, the matrix is not a cement. According to one embodiment, the matrix is not a gel. In the present invention the term "gel" refers to any three-dimensional network of a solid dispersed in a liquid. In one embodiment, the matrix is not a hydrogel (i.e. a gel comprising water molecules). According to one embodiment, the matrix is not a crosslinked polymer. According to one embodiment, the matrix does not comprise a crosslinked polymer. According to one embodiment, the matrix is not a stent. According to one embodiment, the matrix does not comprise silica or its derivatives. According to one embodiment, the matrix does not comprise any bioglass. According to one embodiment, the connective tissue regenerative material does not comprise any metal. According to one embodiment, the connective tissue regenerative material is not a multilayer material. In one embodiment, the connective tissue regenerative material does not comprise any cell growth factor.

According to one embodiment, the matrix comprises at least one polymer selected from biodegradable and/or biocompatible polymer. In one embodiment, the matrix comprises at least one polymer able to be hydrolytically or enzymatically cleaved; preferably said polymer is selected from polyesters, polysaccharides, polypeptides and proteins; more preferably from the group selected from chitosan, chitin, alginate, collagen, hyaluronic acid, poly(lactic acid), poly(glycolic acid), poly(caprolactone), gelatin or any copolymers thereof. In one embodiment, the polymer matrix is chitosan or a mixture of chitosan and alginate. In one embodiment, the polymer matrix is chitosan or a copolymer of chitosan and alginate. According to one embodiment, the polymer matrix is a commercial polymer matrix, preferably is a commercial hemostatic sponge, more preferably is selected from Hemocollagene®, HemCom® and Gel Spon®. According to one embodiment, the matrix comprises at least one polymer selected from biodegradable and/or biocompatible polymer, said polymer precipitating in an aqueous solution having a pH above 6.5, preferably above 7. According to one embodiment, the matrix comprises at least one polymer selected from biodegradable and/or biocompatible polymer, said polymer precipitating in an aqueous solution comprising from 0.5 to 3% wt. of an acid such as acetic acid, having a pH above 6.5, preferably above 7.

According to one embodiment, when the material of the invention is implanted, calcium silicate particles such as $C_3S$ and/or $C_2S$, are hydrated and the matrix of the invention stabilizes the medium pH during the hydration reaction.

In one embodiment, the matrix comprises at least one biopolymer, i.e. a polymer resulting from biomass; preferably the biopolymer is a polysaccharide; more preferably selected from fructans such as inulin, graminan, levan and neo-inulin; glucans such as dextran, floridean starch, glycogen, pullulan, starch, cellulose, chrysolaminarin, curdlan, laminarin, lentinan, lichenin, oat beta-glucan, pleuran and zymosan; galactans such as agar and galactoologosaccharides; and chitin.

In one embodiment, the biopolymer is a glycosaminoglycan; preferably is from the group selected from heparin, heparin sulfate, chondroitin, dermatan sulfate, keratan sulfate and hyaluronic acid or any copolymers thereof.

According to one embodiment, the polymer is a polyvinyl alcohol (PVA). In one embodiment, the polymer is a homopolymer or a copolymer of polyvinyl alcohol (PVA).

According to one embodiment, the polymer is not a starch based polymer. According to one embodiment, the polymer is not a corn starch based polymer. According to one embodiment, the polymer is not a blend comprising a starch based polymer. According to one embodiment, the polymer is not selected from blend of a starch based polymer with ethylene vinyl alcohol, cellulose acetate and/or polycaprolactone. According to one embodiment, the polymer is not selected from blend of a corn starch with ethylene vinyl alcohol, cellulose acetate and/or polycaprolactone. According to one embodiment, the polymer is not a copolymer such as poly(lactic acid-co-glycolic acid). According to one embodiment, the polymer is not selected from polylactic acid, polyglycolic acid, polycaprolactone, polyhydroxy fatty acid esters and their copolymers.

According to one embodiment, the polymer is not selected from starch based polymer such as corn starch based polymer, poly(lactic acid-co-glycolic acid), polylactic acid, polyglycolic acid, polycaprolactone, polyhydroxy fatty acid esters and their copolymers, or any blend comprising a starch based polymer with ethylene vinyl alcohol, cellulose acetate and/or polycaprolactone.

According to one embodiment, the polymer is under the form of a powder or of fibers. According to one embodiment, fibers, preferably polymer fibers, more preferably alginate fibers, strengthen the matrix. According to one embodiment, the amount of fibers in the matrix allows modulating the mechanical properties of the material of the invention. According to one embodiment, fibers are aramid, preferably aramid fibers from Schwarzwalder Textil-Werke®.

According to one embodiment, fibers are poly(vinyl alcohol) (PVA), preferably PVA fibers from Schwarzwalder Textil-Werke®.

According to one embodiment, the polymer is a homopolymer or a copolymer. In one embodiment, the polymer is selected from linear, branched or cross-linked polymer; preferably, the polymer is linear. In one embodiment, the polymer is selected from regular, block, random or graft copolymer. According to one embodiment, the polymer is selected from biodegradable and/or biocompatible polymers which precipitate in an aqueous solution having a pH above 6.5, preferably above 7. According to one embodiment, the polymer is selected from biodegradable and/or biocompatible polymers which precipitate in an aqueous solution comprising from 0.5 to 3% wt. of an acid such as acetic acid, having a pH above 6.5, preferably above 7.

According to one embodiment, the polymer has a mass average molar mass ranging from 5,000 to 1,000,000 g/mol; preferably from 7,000 to 800,000 g/mol, preferably from 10,000 to 700,000 g/mol, more preferably from 20,000 to 600 000 g/mol, more preferably from 30,000 to 500,000 g/mol, more preferably from 100,000 to 500,000 g/mol, more preferably from 150,000 to 300,000 g/mol.

According to one embodiment, the chitosan has a deacetylation degree ranging from 50% to 100%; preferably from 50% to 95%, preferably from 60% to 90%, preferably from 70% to 85%, more preferably from 75% to 85%. In one embodiment, the chitosan has a deacetylation degree higher than 95%. In one embodiment, the chitosan has a deacetylation degree ranging from 95% to 100%, preferably 95%, 96%, 97%, 98%, 99% or 100%.

According to one embodiment, the polymer is a synthetized, hemi-synthetized or bio-sourced polymer (i.e. biopolymer); preferably, bio-sourced. In one embodiment, the polymer may be bio-sourced from animal or vegetable. In one embodiment, the polymer is chitin bio-sourced from fungi, from crab and/or from shrimp. In one preferred embodiment, the biopolymer is chitin bio-sourced from fungi.

According to one embodiment, the matrix is rigid.

In one embodiment, the matrix has interconnected pores; preferably interconnected macropores.

In one embodiment, the pores of the matrix have an average diameter higher than 50 µm; preferably ranging from 75 µm to 900 µm; preferably ranging from 75 µm to 750 µm; more preferably ranging from 100 µm to 400 µm; more preferably ranging from 100 µm to 300 µm; and the calcium silicate particles have $d_{50}$ granulometry ranging from 0.1 µm to 50 µm; preferably, from 5 µm to 40 µm; preferably, from 10 µm to 25 µm; more preferably, about 10 µm. In one embodiment, the calcium silicate particles have $d_{50}$ granulometry ranging from 1 µm to 30 µm.

According to one embodiment, the pores of the matrix have an average diameter higher than 50 µm; preferably ranging from 75 µm to 900 µm; preferably ranging from 75 µm to 750 µm; more preferably ranging from 100 µm to 400 µm; more preferably ranging from 100 µm to 300 µm; and the calcium silicate particles have a $d_{50}$ granulometry ranging from 0.5 µm to 25 µm; preferably from 1 µm to 10 µm; more preferably from 1 µm to 5.5 µm; more preferably from 2 to 4 µm. In one embodiment, the calcium silicate particles have $d_{50}$ granulometry ranging from 3 µm to 4 µm. In one embodiment, the calcium silicate particles are micronized particles.

According to one embodiment, the matrix is a well-ordered matrix; preferably the matrix is structured in sheets. In one embodiment, the matrix is structured in parallel sheets. In one embodiment, the inter-sheet distance ranges from 10 to 300 µm; preferably from 50 to 150 µm. In one embodiment, the thickness of the sheet ranges from more than 0 to 300 µm; preferably ranging from 0.1 µm to 150 µm, preferably from 0.1 µm to 50 µm, preferably, from 0.1 µm to 5 µm; more preferably, the thickness is about 1 µm. In one embodiment, the inter-sheet distance is affected by the choice of the polymer of the polymer matrix.

According to one embodiment, the matrix and/or the regenerative material of the invention has a compression modulus ranging from more than 0 to 1000 kPa, preferably ranging from 0.1 kPa to 900 kPa, more preferably ranging from 200 kPa to 700 kPa. According to one embodiment, the matrix and/or the regenerative material of the invention has a compression modulus ranging from more than 1 to 1000 kPa, preferably from 100 to 1000 kPa, from 200 to 1000 kPa, from 300 to 1000 kPa, from 400 to 1000 kPa, from 500 to 1000 kPa, from 600 to 1000 kPa, from 700 to 1000 kPa, from 800 to 1000 kPa. In one embodiment, the compression modulus is about 240 kPa, 410 kPa, 520 kPa or 600 kPa. According to one embodiment, the compression test was carried out by a rheometer Anton Paar MCR102 using a C-PP25 mobile.

According to one embodiment, the matrix and/or the regenerative material of the invention has a compression strength ranging from more than 0 to 100 MPa, preferably from 0.1 MPa to 50 MPa, more preferably from 0.5 to 5 MPa. According to one embodiment, the matrix and/or the regenerative material of the invention has a compression strength ranging from 0.5 to 2 MPa; from 0.6 to 2 MPa, from 0.7 to 2 MPa; from 0.8 to 2 MPa; from 0.9 to 2 MPa; from 1.0 to 2 MPa; from 1.1 to 2 MPa; from 1.2 to 2 MPa; from 1.3 to 2 MPa; from 1.4 to 2 MPa; from 1.5 to 2 MPa; from 1.6 to 2 MPa; from 1.7 to 2 MPa; from 1.8 to 2 MPa.

According to one embodiment, the compressive strength before C3S loading is 0.5; 0.8 or 0.9 MPa. According to one embodiment, the compressive strength after C3S loading is 1.3 or 1.5 MPa.

According to one embodiment, the non-hydrated calcium silicate particles are selected from dicalcium silicate particles, tricalcium silicate particles (C3S) or any mixtures thereof; preferably, the calcium silicate particles are tricalcium silicate. In one embodiment, the calcium silicate particles do not comprise any phosphate. In one embodiment, the calcium silicate particles do not comprise calcium phosphate. In one embodiment, the calcium silicate particles do not comprise bioglass compounds. In one embodiment, the calcium silicate particles do not comprise metal. In one embodiment, the calcium silicate particles do not comprise hydroxyapatite. According to one embodiment, the non-hydrated calcium silicate particles are not monocalcium silicate ($CaSiO_3$ or wollastonite).

According to one embodiment, the matrix does not comprise any sodium silicate. According to one embodiment, the matrix does not comprise calcium chloride ($CaCl_2$). According to one embodiment, the matrix does not comprise any drugs and/or growth factors. According to one embodiment, the matrix does not comprise isoniazid, rifampicin, gentamicin, bone morphogenetic protein 1 (BMP-1), bone morphogenetic protein 2 (BMP-2), bone morphogenetic protein 7 (BMP-7), bone morphogenetic protein 14 (BMP-14), transforming growth factor alpha (TGF-alpha) and transforming growth factor beta (TGF-beta).

In one embodiment, a powder mixture provides the non-hydrated calcium silicate particles of the invention. For example, the powder mixture is Mineral Trioxide Aggregate (MTA) particles or Portland cement such as Pro Root MTA canal Repair® material (manufactured by Dentsply).

In one embodiment, MTA particles comprise tricalcium silicate, dicalcium silicate and optionally bismuth oxide. In one embodiment, MTA particles comprise about 22% of bismuth oxide in weight to the total weight of MTA particle.

According to one embodiment, the calcium silicate particles are not core-shell particles. In one embodiment, the calcium silicate particles are not porous.

According to one embodiment, the connective tissue regenerative material comprises more than 0% to less than 100%; preferably from 1% to 99%, preferably from 5% to 95%, preferably from 5% to 90%, preferably from 10% to 90%, preferably from 20% to 80%, preferably from 30% to 80%, preferably from 40% to 80%, preferably from 50% to 80%, more preferably from 60% to 70% of calcium silicate particles in weight to the total weight of said connective tissue regenerative material.

According to one embodiment, the connective tissue regenerative material comprises from more than 0% to 300%, preferably from 10% to 280%, more preferably from 20% to 250% of calcium silicate particles in weight to the total weight of the polymer matrix.

According to one embodiment, the connective tissue regenerative material of the invention has a structure of parallel sheets covered by the calcium silicate particles. In one embodiment, the coating of the calcium silicate particles on the matrix sheet, is homogeneously distributed. In one embodiment, the coating of the calcium silicate particles is a monolayer.

According to one embodiment, the connective tissue regenerative material further comprises at least one additive; preferably selected from radio-opacifiers, mineral additives and pigments; more preferably selected from radio-opacifiers and pigments.

According to one embodiment, the connective tissue regenerative material further comprises fibers.

In one embodiment, the connective tissue regenerative material further comprises at least one radio-opacifier; preferably selected from bismuth oxide, strontium carbonate, strontium phosphate, barium sulfate, tantalum oxide, cerium oxide, tin oxide, zirconium oxide compounds; more preferably zirconium oxide in combination with yttrium and radioopaque glasses containing tantalum, barium and strontium, and mixtures thereof; preferably the radio-opacifier is a bismuth derivative, such as for example bismuth oxides or bismuth carbonates or mixture thereof, or zirconium derivative, especially zirconium oxide alone or in combination with yttrium; or a mixture of bismuth derivatives and zirconium derivatives; preferably the radio-opacifier is selected from zirconium oxide and/or bismuth oxide. Radio-opacifiers increase the radio-opacity of the material of the invention, and thus enabling radiographic checking of the restoration and/or regeneration carried out over time.

In one embodiment, the connective tissue regenerative material further comprises at least one pigment; preferably an iron oxide. In one embodiment, said iron oxide is selected from yellow, red and brown iron oxide.

In one embodiment, the connective tissue regenerative material further comprises at least one mineral additive.

Without willing to be bound by any theory, the Applicant evidenced that calcium silicate particles inside the biopolymer matrix both favors reinforcement of mechanical properties of the restoration material and favors cell differentiation in osteoblasts (i.e. cells responsible for bone formation) without the need of adding any cell growth factors.

Especially, in the present invention, the connective tissue regenerative material needs to be anhydrous until used.

Indeed, in the process for manufacturing a regenerative material having a biodegradable polymer matrix such as chitosan, it is required to solubilize the polymer in an aqueous solution having a pH lower than 6.5 in order to avoid the precipitation of said polymer.

However, tricalcium silicate (C3S) reacts with water for providing calcium silicate hydrate (CSH):

$$2Ca_3SiO_5 + 6H_2O \longrightarrow 3CaO \cdot 2SiO_2 \cdot 3H_2O + 3Ca(OH)_2$$
$$\text{C3S} \qquad\qquad\qquad \text{CSH}$$

CSH is a product of the general formula $mCaO.nSiO_2.pH_2O$ wherein n and m, independently ranges from 1 to 3, and p ranges from 3 to 6. In the present invention, CSH is the active compound that improves mechanical properties of the regenerative material. In the present invention, CSH and $Ca(OH)_2$ further provide mineralization properties of the material when placed in a biologic environment.

During the hydration of C3S, the pH of the medium becomes more and more basic.

Consequently, there is a need for providing a process enabling loading calcium silicate particles in a chitosan matrix while avoiding its precipitation during the process.

Advantageously, the process of the invention overcomes this drawback. Advantageously, when placed in a physical environment, the hydration of the connective tissue regenerative material of the invention allows:
modulating the resorption kinetic of the material;
favoring its osteoinductive properties; and
improving its mechanical properties by hardening the implanted material.

Advantageously, the process of the invention allows loading C3S particles in a porous polymer matrix without clogging its pores.

Process for Manufacturing Connective Tissue Regenerative Material

The invention also relates to a process for manufacturing connective tissue regenerative material as described above, comprising a step for contacting an anhydrous porous polymer matrix with a suspension of non-hydrated calcium silicate particles in an anhydrous polar solvent (called step (iv)).

According to one embodiment, the process of invention comprises only one step for contacting an anhydrous porous polymer matrix with a suspension of calcium silicate particles in an anhydrous polar solvent.

According to one embodiment, the process further comprises a preliminary step for preparing the anhydrous porous polymer matrix, said step comprising:
(i) preparing an aqueous solution comprising:
at least one polymer, preferably a biodegradable and/or biocompatible polymer; and
optionally an acid;
(ii) pouring the solution in a mold;
(iii) removing water from the solution in the mold.

According to one embodiment, the process of the invention comprises the following steps:
preparing an aqueous solution of alginate (2%), chitosan (2%) and acetic acid (1%);
freezing and lyophilizing in a mold the solution obtained at the previous step in order to obtain an anhydrous porous polymer matrix; and
contacting said anhydrous porous polymer matrix with a suspension of non-hydrated calcium silicate particles, preferably non-hydrated tricalcium silicate particles, in an anhydrous polar solvent such as acetonitrile.

According to one embodiment, the process does not comprise the use of a silicon compound. According to one embodiment, the process does not comprise the use of 3D printing machine.

Step (i)

According to one embodiment, the step (i) is implemented at a temperature ranging from 15° C. to 50° C.; preferably, from 20° C. to 35° C.; more preferably, the step (i) is implemented at a temperature of about 20° C.

In one embodiment, the step (i) is implemented at atmospheric pressure. In one embodiment, the step (i) is implemented at a pressure equal to about 1 bar.

In one embodiment, the step (i) is implemented under magnetic stirring. In one embodiment, the magnetic stirring of step (i) is of 100 rpm to 500 rpm, preferably from 200 rpm to 500 rpm, preferably from 300 rpm to 500 rpm, or preferably from 400 rpm to 500 rpm. In one embodiment, the magnetic stirring of step (i) is of 100 rpm to 500 rpm, preferably from 300 rpm to 400 rpm, from 310 rpm to 400 rpm, from 320 rpm to 400 rpm, from 310 rpm to 400 rpm, from 320 rpm to 400 rpm, from 330 rpm to 400 rpm, from 340 rpm to 400 rpm, from 350 rpm to 400 rpm, from 360 rpm to 400 rpm, from 370 rpm to 400 rpm, from 380 rpm to 400 rpm, or from 390 rpm to 400 rpm. In one embodiment, the magnetic stirring of step (i) is of 350 rpm.

According to one embodiment, the aqueous solution comprises at least one polymer selected from biodegradable and/or biocompatible polymer. In one embodiment, the matrix comprises at least one polymer able to be hydrolytically or enzymatically cleaved; preferably said polymer is selected from polyesters, polysaccharides, polypeptides and proteins; more preferably from the group selected from chitosan, chitin, alginate, collagen, hyaluronic acid, poly (lactic acid), poly(glycolic acid), poly(caprolactone), gelatin or any copolymers thereof. In one embodiment, the polymer matrix is chitosan or a mixture of chitosan and alginate. In the present invention, the polymer is particularly suitable for its implantation in the body of human or animal. According to one embodiment, the aqueous solution does not comprise halogenated compounds. According to one embodiment, the aqueous solution does not comprise methylene chloride.

In one embodiment, the aqueous solution comprises at least one biopolymer, i.e. a polymer resulting from biomass; preferably the biopolymer is a polysaccharide; more preferably selected from fructans such as inulin, graminan, levan and neo-inulin; glucans such as dextran, floridean starch, glycogen, pullulan, starch, cellulose, chrysolaminarin, curdlan, laminarin, lentinan, lichenin, oat beta-glucan, pleuran and zymosan; galactans such as agar and galactooligosaccharides; and chitin. In one embodiment, the choice of the polymer influences the pore size of the polymer matrix.

In one embodiment, the biopolymer is a glycosaminoglycan; preferably is from the group selected from heparin, heparin sulfate, chondroitin, dermatan sulfate, keratan sulfate and hyaluronic acid or any copolymers thereof.

In one embodiment, the polymer of step (i) is a homopolymer or a copolymer. In one embodiment, the polymer is selected from linear, branched or cross-linked polymer; preferably, the polymer is linear. In one embodiment, the polymer is selected from regular, block, random or graft copolymer.

In one embodiment, the polymer of step (i) has a mass average molar mass ranging from 5,000 to 1,000,000 g/mol; preferably from 7,000 to 800,000 g/mol, preferably from 10,000 to 700,000 g/mol, more preferably from 20,000 to 600 000 g/mol, more preferably from 30,000 to 500,000 g/mol, more preferably from 100,000 to 500,000 g/mol, more preferably from 150,000 to 300,000 g/mol.

In one embodiment, the polymer of step (i) is a synthetized, hemi-synthetized or bio-sourced polymer (i.e. biopolymer); preferably, bio-sourced. In one embodiment, the polymer of step (i) may be bio-sourced from animal or vegetable. In one embodiment, the polymer of step (i) is chitin bio-sourced from mushroom, from crab and/or from shrimp.

In one embodiment, the aqueous solution comprises from 0.5% to 6% of at least one polymer; preferably, from 1% to 5%; more preferably, from 2% to 4%, in weight to the total weight of the aqueous solution. In one embodiment, the aqueous solution comprises from 0.5% to 10% of at least one polymer; preferably from 1% to 10%, from 2% to 10%, from 3% to 10%, from 4% to 10%, from 5% to 10%, from 6% to 10%, from 7% to 10%, from 8% to 10%, or from 9% to 10%, in weight to the total weight of the aqueous solution. In one embodiment, the aqueous solution comprises 1%, 2%, 3%, 4%, 5%, 6%, 7%, 8%, 9%, or 10% of at least one polymer in weight to the total weight of the aqueous solution.

In one embodiment, the aqueous solution further comprises an acid (mineral or organic acid); preferably an organic acid; more preferably, acetic acid. In one embodiment, the organic acid comprises any acid having a carboxyl group (—COOH) and/or a sulfonic (—SO$_3$H) group. In one embodiment, the mineral acid comprises for example hydrochloric acid (HCl), nitric acid (HNO$_3$), phosphoric acid (H$_3$PO$_4$), sulfuric acid (HSO$_4$), boric acid (H$_3$BO$_3$), hydrofluoric acid (HF), hydrobromic acid (HBr), perchloric acid (HClO$_4$) and hydroiodic acid (HI). In one embodiment, the acid is not an amino acid.

In one embodiment, the aqueous solution comprises from 0.5 to 2% of acid, preferably an organic acid, in weight to the total weight of said aqueous solution. In one embodiment, the aqueous solution comprises from 0.5 to 3% of acid, preferably an organic acid, in weight to the total weight of said aqueous solution. In one embodiment, the aqueous solution comprises from 0.5 to 3% of acid, preferably from 0.6 to 3%, from 0.7 to 3% of acid, from 0.8 to 3%, from 0.9 to 3% of acid, from 1 to 3% of acid, from 1.1 to 3% of acid, from 1.2 to 3%, from 1.3 to 3%, from 1.4 to 3%, from 1.5 to 3%, from 1.6 to 3%, from 1.7 to 3%, from 1.8 to 3%, from 1.9 to 3%, from 2 to 3%, from 2.1 to 3%, from 2.2 to 3%, from 2.3 to 3%, from 2.4 to 3%, from 2.5 to 3%, from 2.6 to 3%, from 2.7 to 3%, from 2.8 to 3%, or from 2.9 to 3%, in weight to the total weight of said aqueous solution.

According to one embodiment, the step (i) further comprises addition of additives into the aqueous solution as defined above. In one embodiment, the additive is selected from radio-opacifiers and pigments.

In one embodiment, the radio-opacifier is selected from bismuth oxide, strontium carbonate, strontium phosphate, barium sulfate, tantalum oxide, cerium oxide, tin oxide, zirconium oxide compounds; more preferably zirconium oxide in combination with yttrium and radioopaque glasses containing tantalum, barium and strontium, and mixtures thereof; preferably the radio-opacifier is a bismuth derivative, such as for example bismuth oxides or bismuth carbonates or mixture thereof, or zirconium derivative, especially zirconium oxide alone or in combination with yttrium; or a mixture of bismuth derivatives and zirconium derivatives; preferably the radio-opacifier is selected from zirconium oxide and/or bismuth oxide. Radio-opacifiers increase the radio-opacity of the material of the invention, and thus enabling radiographic checking of the restoration and/or regeneration carried out over time.

In one embodiment, the additive is a pigment; preferably an iron oxide. In one embodiment, said iron oxide is selected from yellow, red and brown iron oxide.

According to one embodiment, the step (i) comprises:
(i-1) mixing an acid such as acetic acid, in an aqueous solution;
(i-2) adding the polymer to the solution obtained at step (i-1);
(i-3) optionally, stirring the mixture obtained at step (i-2).

Step (ii)

According to one embodiment, the mold is a blister pack, preferably a blister pack comprising at least one well, more preferably a preferably a blister pack comprising at least one wells. According to one embodiment, the volume of the mold well is from 1 ml to 10 ml, preferably from 2 ml to 5 ml, more preferably is 3 ml.

According to one embodiment, the step (ii) further comprises a step for degassing the solution obtained from step (i).

Step (iii)

According to one embodiment, the step (iii) is implemented only once.

According to one embodiment, the means for removing water is selected from, lyophilizer, heat evaporator and vacuum evaporator.

According to one embodiment, the step (iii) is implemented by freezing and lyophilizing the solution in a mold obtained at the step (ii).

According to one embodiment, the step (iii) is implemented by heat or vacuum evaporating the solution in a mold obtained at the step (ii).

According to one embodiment, the step (iii) is implemented at a temperature ranging from −80° C. to 5° C.; preferably, from −50 to 1° C.; preferably from −45° C. to −10° C.; more preferably, the step (iii) is implemented at a temperature of about −40° C. or about −24° C. In one embodiment, the solution obtained from step (i) and/or step (ii) is frozen at a temperature of about −24° C. In one embodiment, the lyophilization is implemented at a temperature of about −40° C. In one embodiment, the lyophilization is implemented at a temperature of about −54° C.

In one embodiment, the step (iii) is implemented at pressure ranging from 5 μbar to 500 μbar.

In one embodiment, the process of the invention comprises only one step of freezing and one step of lyophilizing.

In one embodiment, the form of the mold may be in any geometric form; preferably, rectangular, cubic, spherical or cylindrical.

Step (iv)

According to one embodiment, the step (iv) is implemented at a temperature ranging from 10° C. to 50° C.; preferably, from 15° C. to 35° C.; more preferably, the step (iv) is implemented at a temperature of about 20° C.

In one embodiment, the step (iv) is implemented at atmospheric pressure. In one embodiment, the step (iv) is implemented at a pressure of about 1 bar.

In one embodiment, the suspension comprises from more than 0% to 300%, preferably from 5% to 200%, preferably from 10% to 150%, preferably from 20% to 140%, preferably from 30% to 130%, preferably from 40% to 120%, more preferably from 50 to 100%, of calcium silicate particles in weight to the total weight of said suspension.

In one embodiment, the non-hydrated calcium silicate particles are selected from dicalcium silicate particles, tricalcium silicate particles or any mixtures thereof; preferably, the calcium silicate particles are tricalcium silicate.

In one embodiment, the calcium silicate particles have $d_{50}$ granulometry ranging from 0.1 μm to 50 μm; preferably, from 5 μm to 25 μm; preferably from 10 μm to 40 μm; more preferably, about 10 μm. In one embodiment, the calcium silicate particles have a $d_{50}$ granulometry ranging from 0.5 μm to 25 μm; preferably from 1 μm to 10 μm; more preferably from 1 μm to 5.5 μm; more preferably from 2 to 4 μm. In one embodiment, the calcium silicate particles have $d_{50}$ granulometry ranging from 3 μm to 4 μm. In one embodiment, the calcium silicate particles are micronized particles. In one embodiment, the $d_{50}$ granulometry is about 10 μm.

In one embodiment, the suspension comprises an anhydrous polar solvent; preferably selected from acetonitrile, dichloromethane, tetrahydrofuran, ethyl acetate, dimethylformamide, dimethylsulfoxide, acetone, methanol, ethanol isopropyl alcohol and acetic acid. In one embodiment, the solvent in the suspension is acetonitrile. According to one embodiment, the suspension does not comprise halogenated compounds.

According to one embodiment, the suspension does not comprise methylene chloride.

According to one embodiment, the step (iv) further comprises a step of lyophilizing Material Obtained by the Process The invention also relates to a connective tissue regenerative material that may be obtained by the process of the invention as described above.

Implant

The invention also relates to an implant comprising a connective tissue regenerative material as described above.

According to one embodiment, the connective tissue regenerative material may be directly used as an implant.

Uses

The invention also relates to a connective tissue regenerative material for use in the treatment of connective tissue loss in a patient in need thereof, preferably in the treatment of connective tissue loss of orofacial tissues.

According to one embodiment, orofacial tissues comprise connective tissues such as bone and/or pulp and/or membrane, preferably dentin, bone, natural cement and enamel.

According to one embodiment, the material of invention stimulates the genes expression for osteoblastic differentiation. According to one embodiment, the material of invention stimulates the genes expression for osteoblastic differentiation at early times and/or is maintained at longer times. According to one embodiment, the material of invention stimulates the RNAm expression for RunX2, Dlx5, Col11, ALP, BSP and/or SPP1.

According to one embodiment, the material of invention stimulates the genes expression for osteoblastic differentiation after at least one day, preferably after at least 7 days, more preferably after 21 days. According to one embodiment, the material of invention stimulates the genes expression for osteoblastic differentiation after 7 days, 14 days or 21 days.

According to one embodiment, the material of invention is no cytotoxic regarding human osteoblastic cells.

According to one embodiment, the material of invention increases the ALP activity of human cells, preferably of MSC cells.

According to one embodiment, coloration tests allow evidencing the osteodifferentiation of cells when being contacted with the material of the invention. The coloration tests are well-known by the skilled artisan and may be for example alizarin coloration test, phosphatase alkaline activity (ALP) coloration test, or Von Kossa coloration test.

According to one embodiment, the material of the invention is degraded overtime. According to one embodiment, the material of the invention is degraded after at least one week, preferably after at least two weeks, more preferably after 12 weeks. According to one embodiment, when implanted in situ, the weight loss of the material of invention ranges from 1% to 100%, preferably from 10% to 50% wt, more preferably from 20% to 33% wt. According to one embodiment, when implanted in situ, the weight loss of the material of invention is improved when the polymer matrix comprises both alginate and chitosan.

EXAMPLES

The present invention is further illustrated by the following examples.

Abbreviations

C3S: tricalcium silicate;
g: gram(s);
h: hour(s);
ml: milliliter;
rpm: round per minute;
s: second(s);
SEM: Scanning Electron Microscopy;
U: units of activity;
%: percent.

In the examples, the notation "[formulation X]" refer to a formulation used for providing the porous matrix of the invention; and the notation "[formulation X/Y]" refer to a porous regenerative material of the invention comprising a porous matrix resulting from a formulation X; and wherein said matrix has been loaded with calcium silicate particles noted Y.

For example, "[formulation 15]" refers to a formulation for providing a porous matrix. In the following experiment, "[formulation 15]" is a formulation comprising 2% of chitosan, 2% of alginate and 1% of acetic acid.

The regenerative material "[formulation 15/C3S]" refers to a porous matrix obtained from formulation 15, and then loaded with C3S particles.

Materials and Methods

Scanning Electron Microscopy (SEM)

The samples were previously cut into 5 mm×3 mm blocks. Blocks were then metallized in a platinum plasma chamber. The apparatus is SC7640 Sputter coater; Quorum Technologies, Guelph, ON, Canada.

Samples were observed with a Scanning Electron Microscopy (Zeiss SUPRA 40) equipped with an electron gun filed effect, which limits the effects of charges on the surface of samples.

Spectrophotometry

Samples were analyzed with the apparatus TriStar LB941 (Berthold Technologie). The absorbance measure was carried out at 490 nm.

Bright-Field Microscopic

Cell cultures were observed with the apparatus EVOS® FL Cell Imaging System.

PART 1: CHEMICAL EXAMPLES

Example 1: Porous Biopolymer Matrix

Several formulations have been made for manufacturing porous matrixes (see Table 1). The general protocol is described hereinafter.

TABLE 1

Formulations for manufacturing porous polymer matrix.

| Formulation No. | Nature of polymer | Polymer % in the formulation | Acetic acid (% in the formulation) |
| --- | --- | --- | --- |
| 1 | Chitosan from mushroom | 2 | 1 |
| 2 | Chitosan from shrimp | 2 | 1 |
| 3 | Chitosan from mushroom | 1 | 1 |
| 4 | Chitosan from mushroom | 2 | 2 |
| 5 | Alginate | 2 | 0 |
| 6 | Alginate | 3 | 0 |
| 7 | Chitosan from mushroom/Alginate | 1 (chitosan)/1(alginate) | 0.5 |
| 8 | Chitosan from shrimp/alginate | 2(chitosan)/2(alginate) | 1 |
| 9 | Chitosan from crab/Alginate | 1(chitosan)/1(alginate) | 1 |
| 10 | Alginate | 1 | 0 |
| 11 | Chitosan from crab | 2 | 1.5 |
| 12 | Alginate | 4 | 0 |
| 13 | Chitosan from shrimp | 4 | 1 |
| 14 | Chitosan from shrimp | 4 | 3 |
| 15 | Chitosan from shrimp/alginate | 2(chitosan)/2(alginate) | 1 |
| 16 | Chitosan from shrimp/alginate | 2(chitosan)/2(alginate) | 2 |
| 17 | Chitosan from shrimp/alginate fibers | 2(chitosan)/2(alginate) | 1 |
| 18 | Chitosan from shrimp | 10 | 1.5 |
| 19 | Chitosan from shrimp | 4 | 1 |

General Protocol

A polymer solution was realized by mixing from 1 to 10% wt. of a polymer powder (such as chitosan or chitosan/alginate) into purified water that may optionally comprise from 0.5 to 3% wt of acetic acid. The polymer solution was dispensed into blister packs having a capacity of about 3 ml and then, frozen at about −24° C. or −40° C. for at least 24 h. Finally, the samples were lyophilized for 24 h at 0.05 mbar at a temperature of about −54° C.

An example of chitosan porous biopolymer matrix obtained by the process of the invention is presented on FIG. 1.

Characterization

Figure 2A:
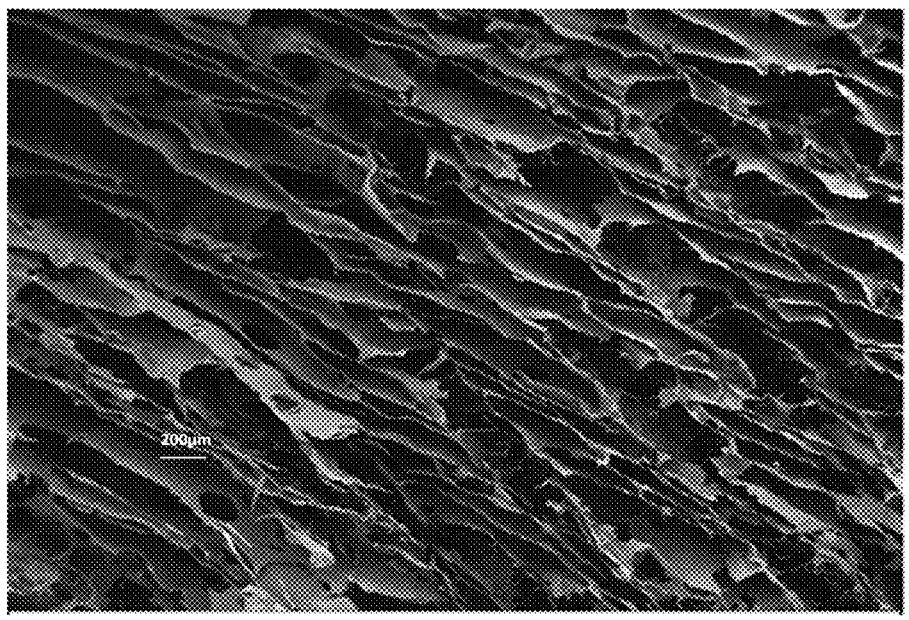
FIGS. 2A and 2B are SEM pictures showing chitosan porous biopolymer matrix with magnification ×100 (2A) or ×500 (2B).
Figure 2B:
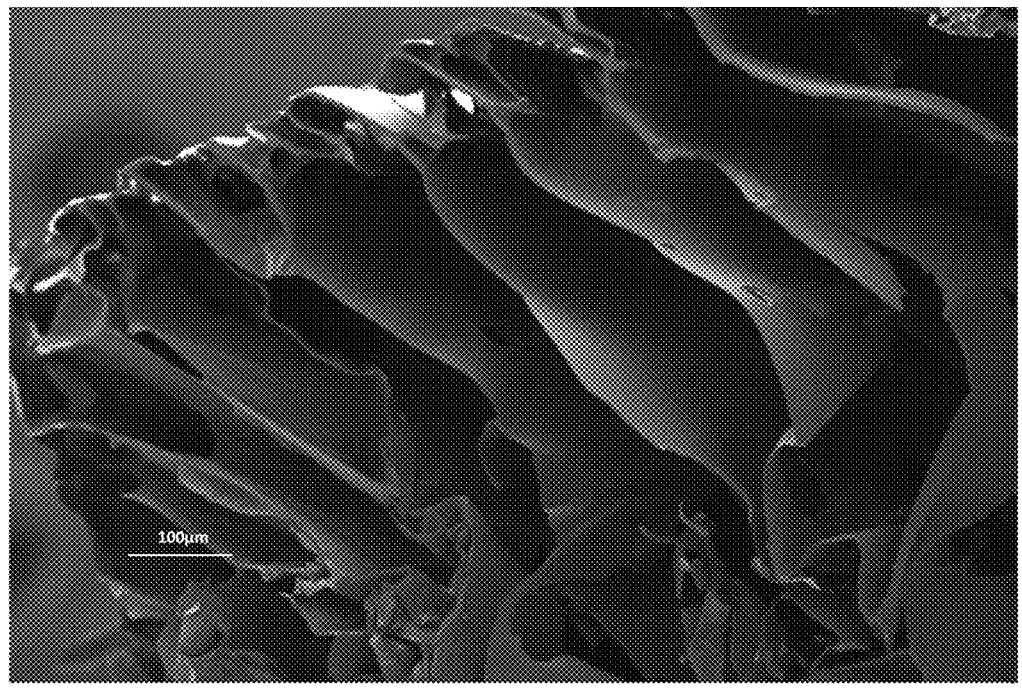

The porous materials were characterized by SEM. The results for a chitosan porous biopolymer matrix (FIGS. 2A and 2B) showed that:
  the matrix is structured in parallel sheets of 1 μm of thickness each;
  the inter-sheets distance is homogeneous;
  the pores are interconnected and each pore has an average diameter ranging from 100 to 300 μm, i.e. higher than the cell diameter;
  the porosity is about 90%.

In conclusion, these results evidence that the porous matrix of the invention is a well-organized and porous structure. Furthermore, the size pore of said matrix may allow the housing of recruited cell when implanted into the body.

Example 2: Synthesis of the Regenerative Material of the Invention

General Protocol

A porous biopolymer matrix obtained as described in Example 1, has been immerged for 30 s into a solution comprising calcium silicate particles suspended in a polar solvent.

The calcium silicate particles may be non-hydrated tricalcium silicate particles (C3S), Biodentine™ powder or mineral trioxide aggregate (MTA) powder. In the examples, MTA particles were Pro Root MTA® canal repair material (manufactured by Dentsply) and had a size ranging from 1 μm to about 30 μm. MTA particles comprise tricalcium silicate, dicalcium silicate and optionally bismuth oxide (about 22%). The solvent may be acetonitrile, ethanol or acetone.

Loaded samples are then dried under vacuum during at least 1 h.

Characterization

Figure 3A:
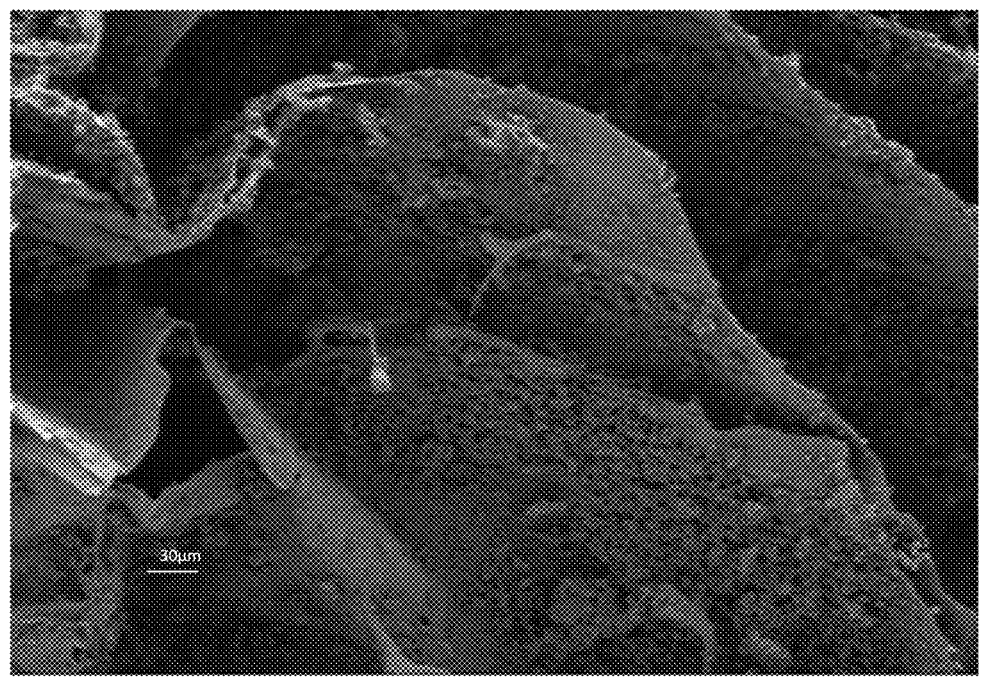
FIGS. 3A and 3B are SEM pictures showing the porous regenerative material obtained by the process of the invention with magnification ×500 (3A) or ×1500 (3B).
Figure 3B:
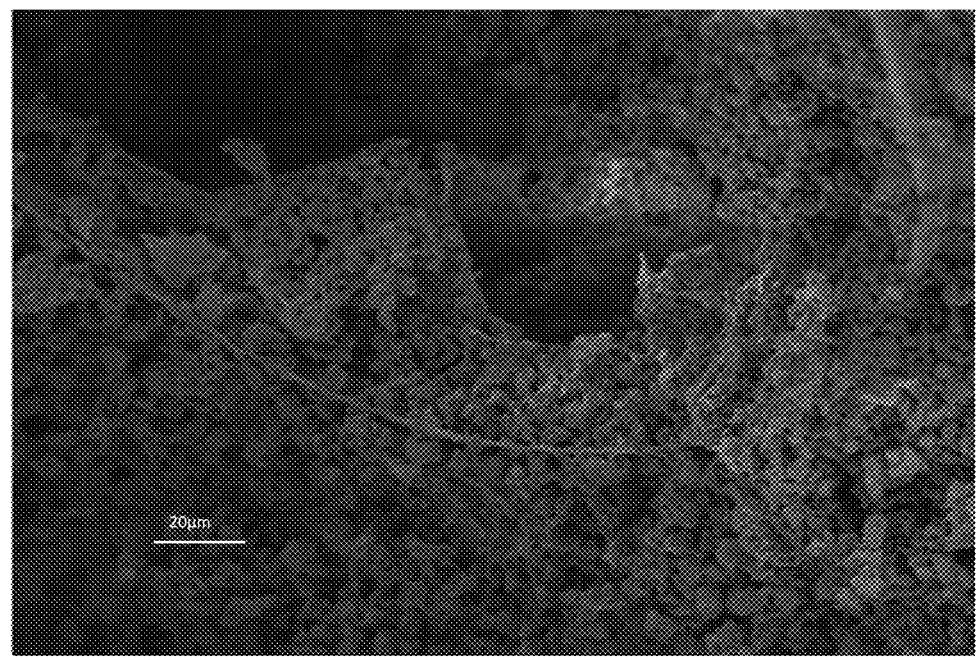

The final materials were characterized by SEM. FIGS. 3A and 3B are presented for porous chitosan materials comprising C3S nanoparticles.

The results show that:
  the impregnation step does not alter the structure of the matrix. The sheets have a thickness of about 2 μm each and the inter-sheet distance ranges from 50 to 150 μm;

C3S particles cover the sheets by providing a thin homogeneous layer inside and outside of the porous matrix; and the pores are still present in the material.

Thus, these experiments evidence that the process of the invention provides a porous material homogenously loaded with tricalcium silicate particles.

Example 3: C3S Loading of Porous Matrix 3.1. From polymer matrix synthetized by the Applicant The aim of this experiment was to show that calcium silicate nanoparticles loading may be modulated into the porous polymer matrix.

For this purpose, a porous matrix (formulation 15 in Table 1: chitosan 2%/alginate 2% and acetic acid 1%) was loaded with a solution comprising 0.5 g, 1 g or 2 g of C3S particles. The protocol is described in Example 2. In this protocol, the solvent was acetonitrile.

Figure 4:
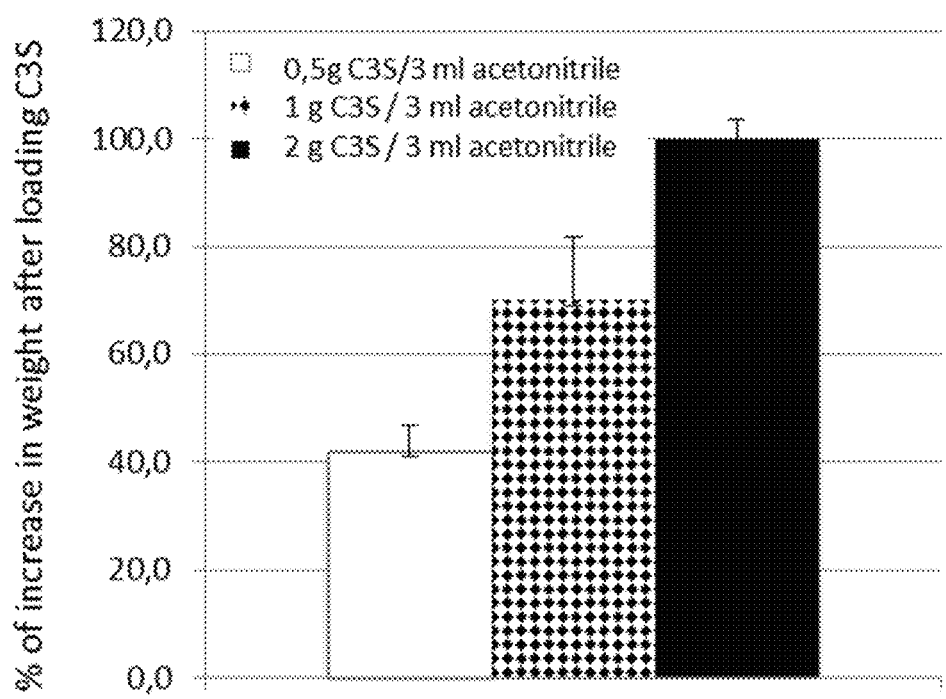
FIG. 4 is a set of histograms showing the increasing percentage of the matrix weight after calcium silicate loading in a chitosan-alginate matrix, said loading being carried out with a suspension of 0.5 g, 1 g or 2 g of C3S particles in 3 ml of acetonitrile.

The results (FIG. 4) evidence that the porous matrix of the invention allows loading C3S particles whatever the concentration of C3S in the loading solution. The results also highlight that the C3S loading may be modulated depending on the concentration of the C3S loading solution.

3.2. From Commercial Hemostatic Sponges

Loading tests have been carried out by contacting a C3S solution (1 mg/ml) with three commercially available hemostatic sponges: Hemocollagene®, HemCom® and GelSpon®. The protocol is described in Example 2.

The results show that for each hemostatic sponge, an efficient C3S loading is achieved.

PART 2: PHYSICO-CHEMICAL TESTS

Example 4: Compression Test 4.1. From Materials Resulting from Formulation 15 (Mixture of Chitosan and Alginate)

This experiment aimed to show that the porous materials of the invention have suitable mechanical properties to be used as implant.

A comparison was carried out between unloaded and calcium silicate loaded porous matrixes obtained from formulation 15 (chitosan 2%/alginate 2% and acetic acid 1%):

TABLE 2

Composition of tested calcium silicate loaded porous matrixes obtained from formulation 15 with different loads.

| Regenerative Material Reference | [Formulation 15] | [Formulation 15/C3S] | [Formulation 15/Biodentine ™] | [Formulation 15/MTA] |
| --- | --- | --- | --- | --- |
| Matrix | Formulation 15 | Formulation 15 | Formulation 15 | Formulation 15 |
| Loading | no | C3S | Biodentine ™ | MTA |

The compression test was carried out by a rheometer Anton Paar MCR102 using a C-PP25 mobile. The following parameters were used:

the speed of descent of the mobile was equal to about 250 µm/s;

the distance from start of measurement (gap) was about 16 mm;

the mobile, during its descent, crushes the sponge and the apparatus measures the normal force (Fn) that the sponge exerts on the mobile (the safety limit for the normal force is 45N).

The results are presented in Table 3.

TABLE 3

Compression modulus for chitosan/alginate porous materials loaded with different calcium silicate particles.

| Material no. | Compression modulus Ec (kPa) |
| --- | --- |
| [Formulation 15] | 240 |
| [Formulation 15/C3S] | 414 |
| [Formulation 15/Biodentine ™] | 584 |
| [Formulation 15/MTA] | 602 |

The results evidence that the addition of calcium silicate compounds, especially comprising tricalcium silicate particles, in the porous matrix allows significantly improved compression modulus, i.e. the mechanical properties of the materials. Depending on the choice of the calcium silicate compound, the compression modulus may be modulated.

4.2. Comparative Tests

The compressive strength has already been studied for materials resulting from formulations 2 and 19, before and after C3S loading. A comparison has been carried out with material resulting from formulation 15.

The results are shown in Table 4.

TABLE 4

Compression strength for chitosan and/or alginate porous materials loaded with different calcium silicate particles.

| Material resulting from: | | Compression strength (MPa) |
| --- | --- | --- |
| Formulation 2 | Before C3S loading | 0.5 |
| | After C3S loading | 1.3 |
| Formulation 15 | Before C3S loading | 0.9 |
| | After C3S loading | 1.9 |
| Formulation 19 | Before C3S loading | 0.8 |
| | After C3S loading | 1.5 |

The results evidence that whatever the polymer matrix formulation, C3S loading increases the mechanical properties of the final materials. The compressive tests also show that better results are achieved for formulation 15, i.e. formulation comprising a mixture of chitosan and alginate.

Example 5: Pores Size of the Polymer Matrix

This experiment aimed to study the pore size for three polymer matrix resulting from:

Formulation 2: chitosan 2% and acetic acid 1%;

Formulation 15: chitosan 2%/alginate 2% and acetic acid 1%; or

Formulation 19: chitosan 4% and acetic acid 1%.

In this goal, SEM pictures have been taken for each of these matrixes.

Figure 7:
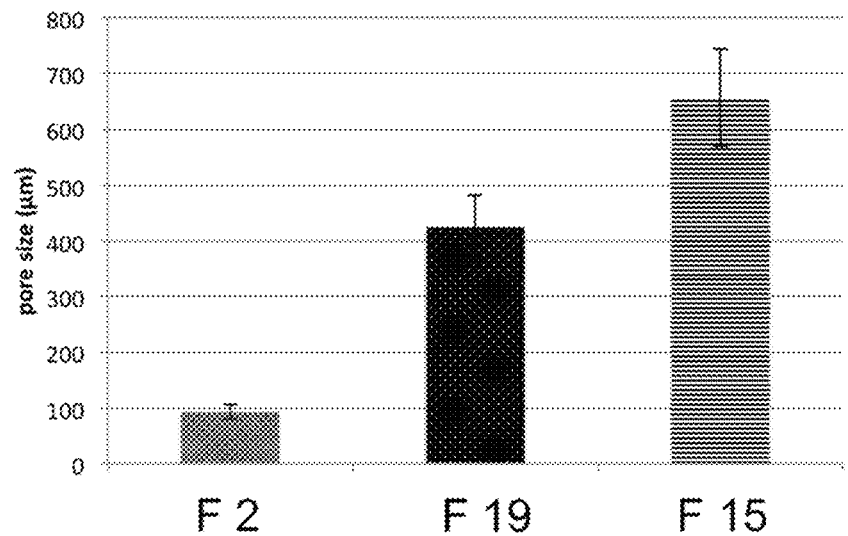
FIG. 7 is a set of histograms showing the pore size for three polymer matrix resulting from formulation 2 (chitosan 2%), formulation 15 (chitosan 2%/alginate 2%) and formulation 19 (chitosan 4%).

The results (FIG. 7) show that:
increasing the polymer concentration in the process of the invention, leads to the increasing the pore size in the final polymer matrix;
when the polymer concentration is of 4%, the pore size is higher for a mixture of 2% of chitosan and 2% of alginate than for formulation comprising 4% chitosan.

In conclusion, this experiment evidences that the increasing of the polymer concentration in the aqueous solution favors the increasing of pore size.

PART 3: BIOLOGICAL TESTS

Example 6: Cytocompatibility Test (MTS)

The aim was to evaluate the resulting cytocompatibility after contacting osteoblastic precursor cells (human bone marrow mesenchymal stem cells (MSC)) with:
either a suspension of C3S particles at a concentration of 1 or 2 mg/ml;
or the regenerative material [formulation 15/C3S] as defined in the previous examples.

Thus, the following tests were carried out:
cells cultured without any adjunction of materials (negative control);
cells cultured in a medium enriched with the material of the invention [Formulation 15/C3S] (at a concentration equals of about 1 or 2 mg/ml); and
cells cultured in a medium enriched with C3S particles (at a concentration equals of about 1 or 2 mg/ml).

Protocol

The test took place in three phases:
(1) After seeding the cells, cells were cultured for 24 h;
(2) The material of the invention [Formulation 15/C3S] or C3S particles were added into the proliferative medium (DMEM, 10% fetal calf serum, 50 UI/ml antibiotics).

The cytocompatibility was evaluated regarding to the time of cells culture with enriched-medium:
a brief contact (24 h) to highlight a putative immediate toxic effect;
an intermediate contact (48 h);
a longer contact (72 h) to demonstrate a putative effect (inhibition or activation) of the material on proliferation.
(3) Cell viability was measured using a spectrophotometer at 490 nm at 24 h, 48 h or 72 h.

Results

Figure 5:
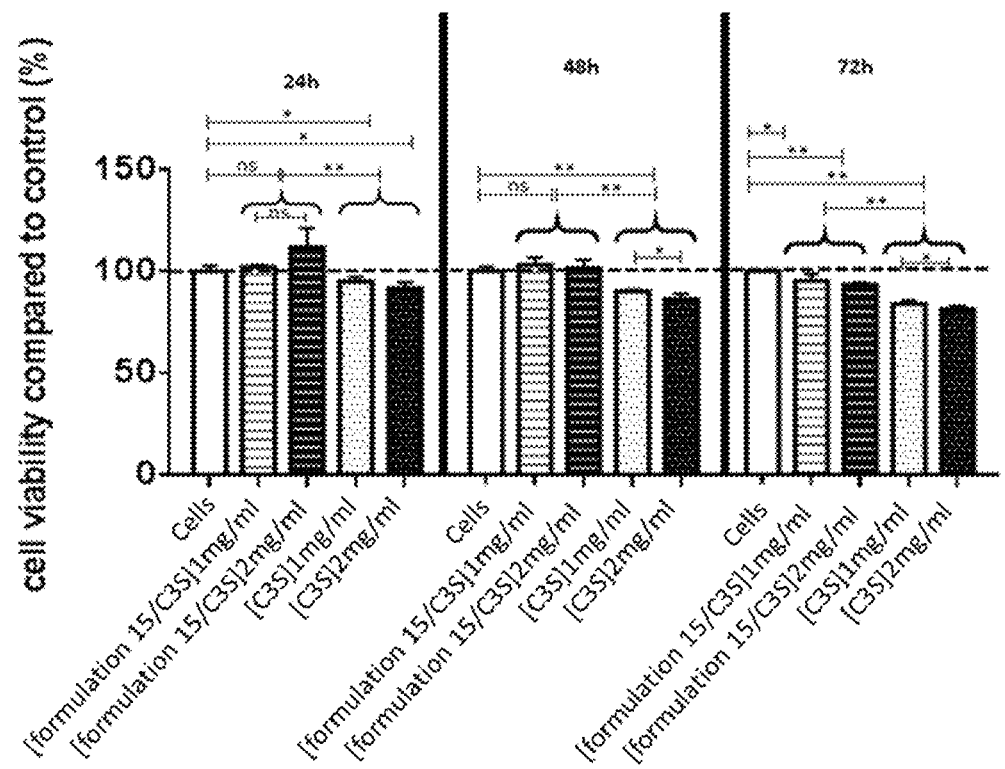
FIG. 5 is a set of histograms showing MTS assay of osteoblastic cells grown with the material of the invention [formulation 15/C3S] at the concentration 1 or 2 mg/ml; and C3S particles at the concentration 1 or 2 mg/ml after 24h, 48h or 72h. Data were expressed as percentages compared against the control. Statistical analysis was performed using the Mann Whitney test (non-parametric) ns: not significant; *$p<0,05$; $p<0,01$;*$p<0,005$.

The results (FIG. 5) evidence that there is no cytotoxicity for the regenerative material of the invention regarding human osteoblastic cells.

Of note, the best results were obtained for the material of the invention resulting from formulation 15 loaded with a concentration of about 2 mg/ml of C3S.

A slight decrease of cell viability was observed for C3S particles. This phenomenon may be attributed to the basicity increasing due to the calcium hydroxide formation during the hydration reaction of C3S particles by the biological medium.

Surprisingly, when C3S particles are loaded into the matrix of the invention, better cell viability is observed suggesting that the matrix of the invention may stabilize the medium pH during the hydration of C3S particles.

Example 7: Osteoblastic Differentiation and Mineralization in Presence of the Materials of the Invention 7.1. Preliminary Test The aim was to evaluate the ability of either the material of the invention [formulation 15/C3S] or C3S particles (1 mg/ml), to stimulate the osteoblastic differentiation.

This experiment was carried out on human bone marrow mesenchymal stem cells (MSC) cultured in enriched mineralizing medium.

Bright-field microscopic pictures were taken at Day 14.

Figure 6:
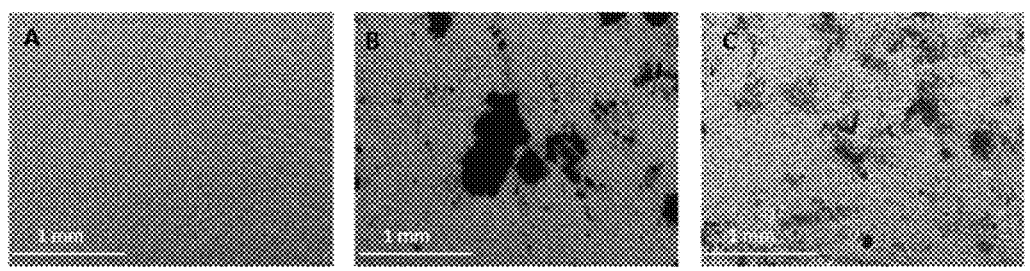
FIGS. 6A, 6B, and 6C are bright-field microscope pictures of osteoblastic cells alone (6A), or grown with the material of the invention [formulation 15/C3S] at 2 mg/ml (6C) or C3S particles at 1 mg/ml (6B) after 14 days of culture.

The results showed that cells grew in direct contact with either the regenerative materials of the invention (FIG. 6C) or C3S particles (FIG. 6B) compared to the cells alone (FIG. 6A). Bone-like mineralized nodules were observed in cells condensation suggesting that the materials of the invention efficiently stimulate the osteodifferentiation of human MSC.

7.2. Coloration Tests

The differentiation ability in osteoblasts for MSC cells was studied in presence of the materials of the invention (Formulation 15). Cells alone (without the materials of the invention) are used for positive control. The colorations were carried out on cell cultures after 7 days, 14 days and 21 days. Bright-field microscopic pictures were taken at 7 days, 14 days and 21 days.

7.2.1. ALP Coloration

The phosphatase alkaline activity (ALP) is one of markers for cell differentiation of stem cells.

Figure 9:
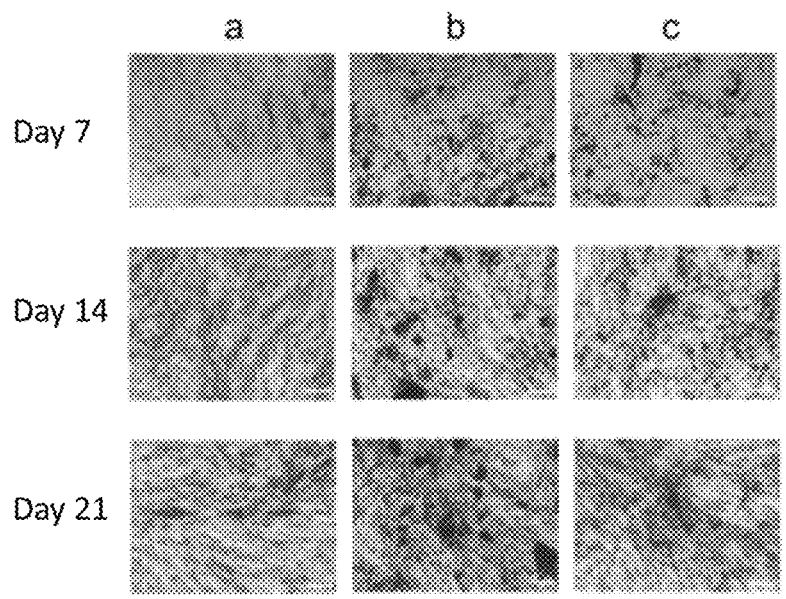
FIG. 9 includes bright-field microscope pictures for ALP coloration of osteoblastic cells alone (a), or grown with the material of the invention [formulation 15/C3S] at 2 mg/ml (b) or C3S particles at 1 mg/ml (c) after 7, 14 or 21 days of culture.

For detecting the phosphatase alkaline activity, ALP colorations were implemented. The results are shown FIG. 9.

These results evidence that the ALP activity is increased when cells are contacted with the materials of the invention.

7.2.2. Von Kossa Coloration

Figure 10:
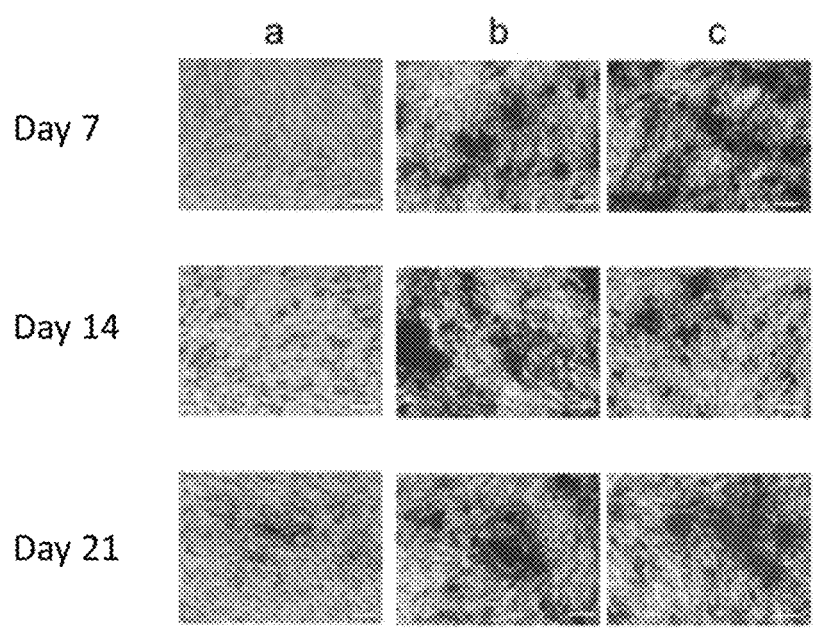
FIG. 10 includes bright-field microscope pictures for Von Kossa coloration of osteoblastic cells alone (a), or grown with the material of the invention [formulation 15/C3S] at 2 mg/ml (b) or C3S particles at 1 mg/ml (c) after 7, 14 or 21 days of culture.

In situ Von Kossa coloration allows highlighting the formation of mineralized nodules, especially calcium crystals. The results are shown FIG. 10.

These results confirm those obtained from ALP coloration.

7.2.3. Alizarin Coloration

Figure 11:
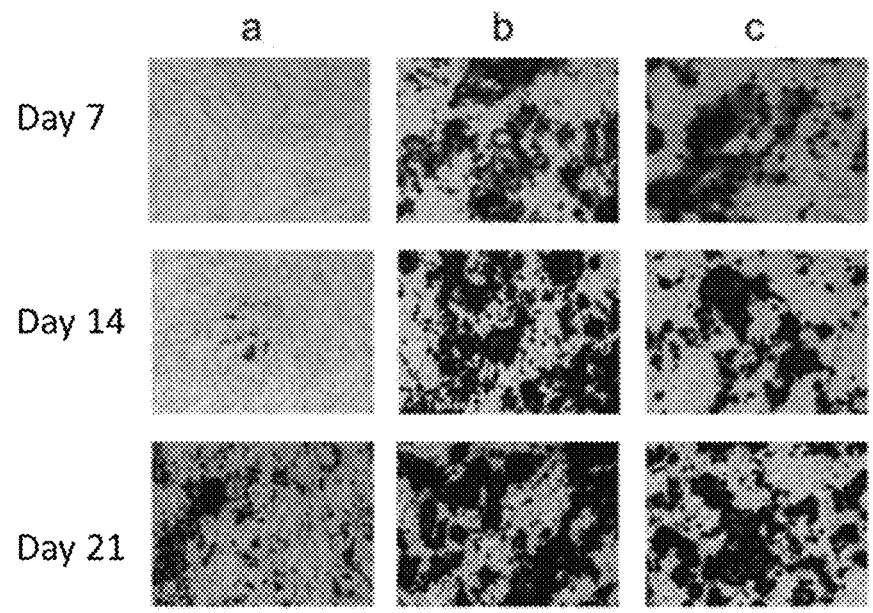
FIG. 11 is bright-field microscope pictures for Alizarin coloration of osteoblastic cells alone (FIG. 11A), or grown with the material of the invention [formulation 15/C3S] at 2 mg/ml (FIG. 11B) or C3S particles at 1 mg/ml (FIG. 11C) after 7, 14 or 21 days of culture.

Alizarin coloration also allows highlighting the formation of mineralized nodules. The results are shown FIG. 11.

From bright-field microscopic pictures, the spectroscopy of the red coloration (420 nm) allows quantifying the mineralized products in the samples.

These results confirm that the differentiation of MSC cells is faster in presence of the materials of the invention.

7.3. General Conclusion

Coloration tests evidence the non-toxicity of the polymer matrix of formulation 15, loading with C3S (at a concentration of 1 mg/ml). No cellular pain is observed overtime and the cells in presence of the material of invention are able to self-organize in a tridimensional structure and synthesize extracellular matrix. Furthermore, the ALP activity and the apparition of bone mineralized nodules show that the material of invention does not damage the osteoblastic differentiation of cells.

Example 8: Degradation Test

Degradation tests were carried out in order to evaluate the resorbability of the materials of the invention.

This study was carried out during 12 weeks, from materials having a polymer matrix resulting from formulations 2, 15 and 19 as described hereinabove.

Before C3S loading, all the materials feature 100% of degradation of their structure after few minutes of solubilisation.

Figure 8:
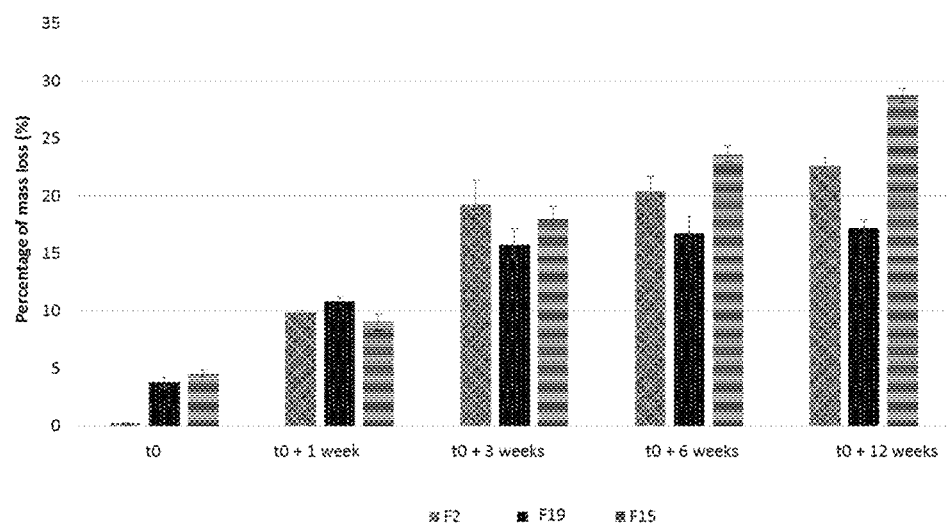
FIG. 8 is a set of histograms showing the degradation during 12 weeks for three polymer matrix resulting from formulation 2 (chitosan 2%), formulation 15 (chitosan 2%/alginate 2%) and formulation 19 (chitosan 4%).

After C3S loading, the evolution of the degradation are shown FIG. 8.

The results evidence that all materials of the invention are degraded overtime: after 12 weeks, the weight loss of the materials ranges from 20% to 33% wt. The set of histograms also feature that improved degradation is achieved for a polymer matrix comprising both alginate and chitosan.

Thus, these results evidence that the materials of the invention are compatible with the kinetics of cell regeneration.

Example 9: Gene Expressions

In order to confirm the results of coloration tests, the expression level of some osteoblastic markers (osteoblastic transcription factors and markers of bone proteins) have been analyzed by Reverse Transcriptase PCR (RT-PCR) at day 7, 14 and/or 21, after MSC cells being contacted with the material of invention resulting from formulation 15 loaded with C3S. A comparison was done between (a) the MSC cells alone in the medium, (b) the MSC cells in presence of the material of the invention in the medium, and (c) the medium only comprising C3S particles.

9.1. Early Differentiating Factors

The RNAm level was quantified for each of the following differentiation factors after 21 days:
RunX2: runt related transcription factor 2;
Dlx5: distal-less homeobox 5;
Col11: collagen 1;
And ALP: alkaline phosphatase.

The results were normalized by the expression of genes RS15 (i.e. 40S ribosomal protein S15) and TBP (TATA-box binding protein).

Figure 12:
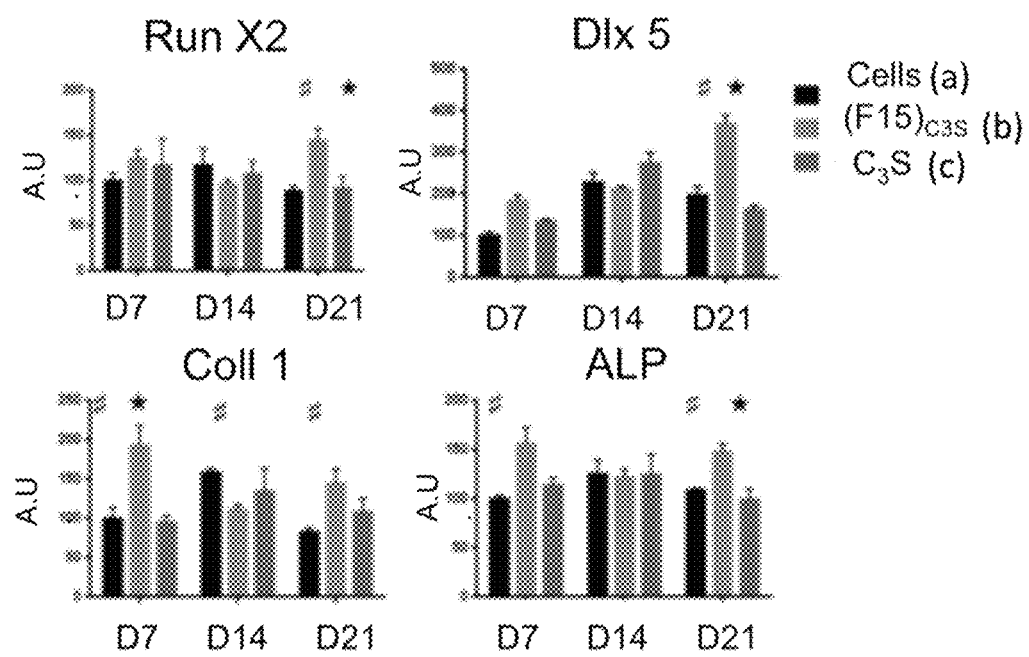
FIG. 12 is a set of histograms showing the RNAm level of RunX2, Dlx5, Col1 and ALP after 21 days for (a) MSC cells alone in the medium, (b) MSC cells in presence of the material of the invention in the medium, and (c) the medium only comprising C3S particles; the material of invention resulting from a polymer matrix of formulation 15 loaded with C3S.

The results (FIG. 12) show that significant differences after 21 days are achieved, between MSC cells (a) alone in the medium, and (b) cells in presence of the material of invention.

9.2. Late Differentiating Factors

The RNAm level was quantified for each of the following differentiation factors after 7, 14 and 21 days:
BSP: Bone sialoprotein;
SPP1: osteopontin.

The results were normalized by the expression of genes RS15 (i.e. 40S ribosomal protein S15) and TBP (i.e. TATA-box binding protein).

Figure 13:
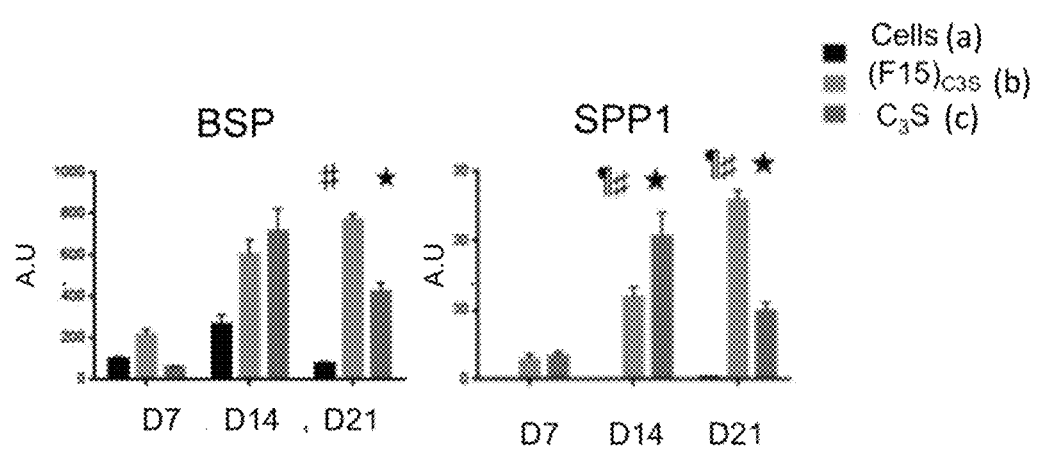
FIG. 13 is a set of histograms showing the RNAm level of BSP and SPP1 after 7, 14 and 21 days for (a) MSC cells alone in the medium, (b) MSC cells in presence of the material of the invention in the medium, and (c) the medium only comprising C3S particles; the material of invention resulting from a polymer matrix of formulation 15 loaded with C3S.

The results (FIG. 13) show that differences are achieved as soon as day 7, between MSC cells (a) alone in the medium, and (b) cells in presence of the material of invention. Especially, significant differentiation is observed after 14 days and 21 days for SPP1, and after 21 days for BSP.

9.3. General Conclusion

The analysis of gene expressions exhibits that the material of invention stimulates the genes expression for osteoblastic differentiation. The results also evidence that this stimulation is carried out at early times and is maintained at longer times.

The invention claimed is:

1. A connective tissue regenerative material, comprising:
a porous polymer matrix having interconnected pores; and
calcium silicate particles;
wherein:
said polymer matrix is anhydrous;
said calcium silicate particles are non-hydrated;
said non-hydrated calcium silicate particles have a $d_{50}$ granulometry ranging from 0.05 µm to less than the average diameter of the pores of the matrix; and
said non-hydrated calcium silicate particles being coated on the inside walls of the pores of the matrix.

2. The connective tissue regenerative material according to claim 1, wherein the connective tissue regenerative material is a bone, dentin or pulp regenerative material.

3. The connective tissue regenerative material according to claim 1, wherein the porous polymer matrix comprises or consists of at least one polymer selected from biodegradable and/or biocompatible polymer.

4. The connective tissue regenerative material according to claim 3, wherein said polymer is selected from polyesters, polysaccharides, polypeptides and proteins.

5. The connective tissue regenerative material according to claim 3, wherein said polymer is selected from chitosan, chitin, alginate, collagen, hyaluronic acid, poly(lactic acid), poly(glycolic acid), poly(caprolactone), gelatin or any copolymers thereof.

6. The connective tissue regenerative material according to claim 3, wherein the polymer is a mixture of chitosan and alginate.

7. The connective tissue regenerative material according to claim 1, further comprising at least one additive.

8. The connective tissue regenerative material according to claim 7, wherein the additive is selected from fibers and radio-opacifiers.

9. The connective tissue regenerative material according to claim 8, wherein the additive is selected from alginate fibers, bismuth oxide, strontium carbonate, strontium phosphate, barium sulfate, tantalum oxide, cerium oxide, tin oxide, zirconium oxide compounds and pigments.

10. The connective tissue regenerative material according to claim 1, wherein the matrix is structured in sheets.

11. The connective tissue regenerative material according to claim 10, wherein the inter-sheet distance ranges from 50 to 150 µm.

12. The connective tissue regenerative material according to claim 1, wherein the calcium silicate particles are selected from dicalcium silicate particles, tricalcium silicate particles or any mixtures thereof.

13. The connective tissue regenerative material according to claim 1, wherein the average pore diameter ranges from higher than 50 µm.

14. A process for manufacturing the connective tissue regenerative material according to claim 1, comprising a step for contacting an anhydrous porous polymer matrix with a suspension of non-hydrated calcium silicate particles in an anhydrous polar solvent.

15. The process according to claim 14, further comprising a preliminary step for preparing the anhydrous porous polymer matrix; said step comprising:
(i) preparing an aqueous solution comprising:
at least one polymer; and
optionally an acid;
(ii) pouring the solution in a mold;
(iii) removing water.

16. The process according to claim 15, wherein the means for removing water is selected from lyophilizer, heat evaporator and vacuum evaporator.

17. The process according to claim 14, wherein when the polymer is chitosan or chitin, the aqueous solution comprises an acid.

18. The process according to claim 14, wherein the polar solvent is selected from acetonitrile, dichloromethane, tetrahydrofuran, ethyl acetate, dimethylformamide, dimethylsulfoxide, acetone, methanol, ethanol isopropyl alcohol and acetic acid.

19. A method for treating connective tissue loss in a patient, comprising implanting the connective tissue regenerative material according to claim 1 in a patient in need thereof.

20. An implant comprising the connective tissue regenerative material according to claim 1.

* * * * *